US006803211B2

(12) United States Patent
Tong et al.

(10) Patent No.: US 6,803,211 B2
(45) Date of Patent: Oct. 12, 2004

(54) METHODS AND COMPOSITIONS FOR DIAGNOSING AND TREATING DISORDERS INVOLVING ANGIOGENESIS

(75) Inventors: Xiao Tong, East Brunswick, NJ (US); Michael G. Sheppard, Victoria (AU)

(73) Assignees: Pfizer Inc., New York, NY (US); Pfizer Products Inc., Groton, CT (US)

(*) Notice: Subject to any disclaimer, the term of this patent is extended or adjusted under 35 U.S.C. 154(b) by 0 days.

(21) Appl. No.: 09/938,391

(22) Filed: Aug. 24, 2001

(65) Prior Publication Data

US 2003/0158099 A1 Aug. 21, 2003

Related U.S. Application Data

(60) Provisional application No. 60/227,924, filed on Aug. 25, 2000.

(51) Int. Cl.[7] .......................... C12P 21/06; C12P 15/63; C12N 5/00; C07H 21/02; C07K 1/00

(52) U.S. Cl. .................. 435/69.1; 435/320.1; 435/325; 435/455; 530/350; 530/351; 536/23.1; 536/23.5

(58) Field of Search ............................ 435/69.1, 320.1, 435/325, 455; 530/350, 351; 536/23.1, 23.5

(56) References Cited

U.S. PATENT DOCUMENTS

| | | | |
|---|---|---|---|
| 4,109,496 A | 8/1978 | Allemann et al. | |
| 4,215,051 A | 7/1980 | Schroeder et al. | |
| 4,376,110 A | 3/1983 | David et al. | |
| 4,656,127 A | 4/1987 | Mundy | |
| 4,683,195 A | 7/1987 | Mullis et al. | |
| 4,683,202 A | 7/1987 | Mullis | |
| 4,816,397 A | 3/1989 | Boss et al. | |
| 4,816,567 A | 3/1989 | Cabilly et al. | |
| 4,851,331 A | 7/1989 | Vary et al. | |
| 4,873,191 A | 10/1989 | Wagner et al. | |
| 4,946,778 A | 8/1990 | Ladner et al. | |
| 5,075,217 A | 12/1991 | Weber | |
| 5,093,246 A | 3/1992 | Cech et al. | |
| 5,225,539 A | 7/1993 | Winter | |
| 5,272,057 A | 12/1993 | Smulson et al. | |
| 5,272,071 A | 12/1993 | Chappel | |
| 5,364,759 A | 11/1994 | Caskey et al. | |
| 5,399,349 A | 3/1995 | Paunescu et al. | |
| 5,459,039 A | 10/1995 | Modrich et al. | |
| 5,498,531 A | 3/1996 | Jarrell | |
| 5,545,806 A | 8/1996 | Lonberg et al. | |
| 5,569,825 A | 10/1996 | Lonberg et al. | |
| 5,585,089 A | 12/1996 | Queen et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 2003/0012792 A1 * | 1/2003 | Holaday et al. | 424/185.1 |
| 2003/0139365 A1 * | 7/2003 | Lo et al. | 514/44 |

FOREIGN PATENT DOCUMENTS

| | | |
|---|---|---|
| EP | 0173494 | 8/1985 |
| EP | 0184187 | 6/1986 |
| EP | 0125023 | 6/1991 |
| EP | 0171496 | 5/1993 |
| WO | 8601533 | 3/1986 |
| WO | 8702671 | 5/1987 |
| WO | 8804300 | 6/1988 |
| WO | 8809810 | 12/1988 |
| WO | 8910134 | 11/1989 |
| WO | 9011364 | 10/1990 |
| WO | 9102087 | 2/1991 |
| WO | 9106667 | 5/1991 |
| WO | 9215712 | 9/1992 |
| WO | 9416101 | 7/1994 |
| WO | 9500669 | 1/1995 |
| WO | 9511995 | 5/1995 |
| WO | 0011033 | 3/2000 |

OTHER PUBLICATIONS

Molema et al, Biochem, Pharmacol. 55:1939–45, 1999.*
Moses Biotech 9:630–634, 1991.*
Ngo, in The Protein Folding Problem and Tertiary Structure Prediction, Merz et al. (eds.), Birkhauser Boston: Boston, MA, pp. 433 and 492–495, 1994.*
Rudinger (in Peptide Hormones, Parsons (ed.), University Park Press: Baltimore, MD, pp. 1–7, 1976.*
PTO Sequence search report Aug. 18, 2003.*
Auerbach, et al.; Angiogenesis Inhibition: A Review; Pharmac. Ther.; vol. 63, pp. 265–311 (1994).
Ribatti, et al.; Angiogenesis under normal and pathological conditions; Haematologica; 76:311–320 (1991).
Risau; Mechanisms of Angiogenesis: Nature 386:671–674 (1997).
Folkman; Angiogenesis in cancer, vascular, rheumatoid and other disease; Nature Medicine; 1(1): 27–31 (1995).
Isner; Cancer and Atherosclerosis; Circulation; 99(13): 1653–1655 (1999).

(List continued on next page.)

*Primary Examiner*—Jeffrey Fredman
*Assistant Examiner*—Sumesh Kaushal
(74) *Attorney, Agent, or Firm*—Lorraine B. Ling; Thomas Wootton; Kohn & Associates, PLLC

(57) ABSTRACT

The present invention relates to polynucleotides associated with angiogenesis-related disorders. The present invention also relates to canine endostatin genes, novel genes associated with angiogenesis-related disorders, such as cancer. The invention encompasses endostatin nucleic acids, recombinant DNA molecules, cloned genes or degenerate variants thereof, endostatin gene products and antibodies directed against such gene products, cloning vectors containing mammalian endostatin gene molecules, and hosts that have been genetically engineered to express such molecules. The invention further relates to methods for the identification of compounds that modulate the expression of endostatin genes and gene products and to using such compounds as therapeutic agents in the treatment of angiogenesis-related disorders, e.g., cancer. The invention also relates to methods for the diagnostic evaluation, genetic testing and prognosis of angiogenesis-related disorders, e.g., cancer, and to methods and compositions for the treatment these disorders.

7 Claims, 10 Drawing Sheets

OTHER PUBLICATIONS

Koch; Arthritis & Rheumatism; Arthritis & Rheumatism; 41(6):951–962 (1998).
Walsh; Angiogenesis and arthritis; Rheumatology; 38(2):103–112 (1998).
Ware, et al.; Angiogenesis in ischemic heart disease; Nature Medicine; 3(2):158–164 (1997).
Folkman; How is blood vessel growth regulated in normal and neoplastic tissue? Cancer Research; 46(2):467–473 (1986).
Folkman; What is the evidence that tumors are angiogenesis dependent; J. of the Nat. Cancer Inst.; 83(1):4–6 (1990).
Folkman; The role of angiogenesis in tumor growth; Seminars in Cancer Biology; 3(2):65–71 (1992).
Zetter; Angiogenesis and tumor metastasis; Annu. Rev. Med.; 49:407–424 (1998).
Folkman; Angiogenesis in cancer, vascular, rheumatoid and other disease; Nat. Med; 1(1):27–31 (1995).
M. S. O'Reilly, et al.; Endostatin: An endogenous inhibitor of angiogenesis and tumor growth; Cell; 88(2):277–285 (1997).
M. S. O'Reilly, et al.; Angiostatin: A novel angiogenesis inhibitor that mediates the suppression of metastases by a lewis lung carcinoma; Cell; 79(2):315–328 (1994).
Boehm, et al.; Antiangiogenic therapy of experimental cancer does not induce acquired drug resistance; Nature; 390(6658):404–407 (1997).
Fidler, et al.; The implications of angiogenesis for the biology and therapy of cancer metastasis; Cell; 79(2):185–188 (1994).
Gasti, et al.; Angiogenesis as a target for tumor treatment; Oncology; 54(3):177–184 (1997).
Van Hinsbergh, et al.; Angiogenesis and anti–angiogenesis: Perspectives for the treatment of solid tumors; Ann. Oncol.; 10 Suppl. 4:60–63 (1999).
Klement, et al.; Continuous low–dose therapy with vinblastine and VEGF receptor–2 antibody induces sustained tumor regression without overt toxicity: The J. of Clinical Invest.; 105(8):R15–24 (2000).
Browder, et al.; Antiangiogenic Scheduling of chemotherapy improves efficacy against experimental drug–resistant cancer; Cancer Research; 60:1878–1886; (2000).
Arap, et al.; Cancer treatment by targeted drug delivery to tumor vasculature in a mouse model; Science; 279(5349):377–380 (1998).
Mauceri, et al.; Combined effects of angiostatin and ionizing radiation in antitumour therapy; Nature; 394(6690):287–291 (1998).
Bronson; Variation in age at death of dogs of different sexes and breeds; Am. J. Vet. Res.; 43(11)2057–2059 (1982).
Bostock; Canine and feline mammary neoplasms; Br. Vet. J.; 142(6):506–515 (1986).
Bostock; Neoplasms of the skin and subcutaneous tissues in dogs and cats; Br. Vet. J.; 142(1):1–19 (1986).
MacEwen; Spontaneous tumors in dogs and cats: Models for the study of cancer biology and treatment; Cancer and Metastasis Reviews; 9(2):125–136 (1990).
Karlin, et al.; Methods for assessing the statistical significance of molecular sequence features by using general scoring schemes; Proc. Natl. Acad. Sci.; 87:2264–2268 (1990).
Karlin, et al.; Applications and statistics for multiple high––scoring segments in molecular sequences; Proc. Natl. Acad. Sci.; 90:5873–5877 (1993).
Altschul, et al.; Basic Local Alignment Search Tool; J. Mol. Biol.; 215:403–410 (1990).
Altschul, et al.; Gapped BLAST and PSI–BLAST: a new generation of protein database search programs; Nucleic Acids Research; 25(17):3389–3402 (1997).
Myer, et al.; Optimal alignments in linear space; CABIOS; 4:11–17 (1988).
Ruther, et al.; Easy identification of cDNA clones; EMBO Journal; 2(10):1791–1794 (1983).
Inouye, et al.; Up–promoter mutations in the Ipp gene of *Escherichia coli*; Nucleic Acids Research; 13(9):3101–3109 (1985).
G. Van Heeke, et al.; Expression of human asparagine synthetase in *Escherichia coli*; The J. of Biological Chemistry; 264:5503–5509 (1989).
Smith, et al.; Molecular engineering of the autographa californica nuclear polyhedrosis virus genome: Deletion mutations within the polyhedron gene; J. of Virology; 46:584–593 (1983).
Logan, et al.; Adenovirus tripartite leader sequence enhances translation of mRNAs late after infection; 81:3655–3659 (1984).
Bitter, et al.; Expression and secretion vectors for yeast; Methods in Enzymology; 153:516–544 (1987).
Wigler, et al.; Transfer of purified herpes virus thymidine kinase gene to cultured mouse cells; Cell; 11:223–232 (1977).
Szybalska, et al.; Genetics of human cell lines, IV: Proc. Natl. Acad. Sci.; 48:2026–2034 (1962).
Lowy, et al.; Isolation of transforming DNA: cloning the hamster aprt gene; Cell; 22:817–823 (1980).
Wigler, et al.; Transformation of mammalian cells with an amplifiable dominant–acting gene; Proc. Natl. Acad. Sci.; 77(6)3567–3570 (1980).
O'Hare, et al.; Transformation of mouse fibroblasts to methotrexate resistance by a recombinant plasmid expressing a prokaryoti dihydrofolate reductase; Proc. Natl. Acad. Sci.; 78:1527–1531 (1981).
Mulligan, et al.; Selection for animal cells that express the *Escherichia coli* gene coding for xanthine–guanine phosphoribosyltransferase; Proc. Natl. Acad. Sci.; 78(4):2072–2076 (1981).
Colbere–Garapin, et al.; A new dominant hybrid selective marker for higher eukaryotic cells: J. Mol. Biol.; 150:1–13 1981).
Santerre, et al.; Expression of prokaryotic genes for hygromycin B and G418 resistance as dominant–selection markers in mouse L cells; Gene; 30:147–156 (1984).
Janknecht, et al.; Rapid and efficient purification of native histidine–tagged protein expressed by recombinant vaccinia virus; Proc. Natl. Acad. Sci.; 88:8972–8976 (1991).
H. Van Der Putten, et al.; efficient insertion of genes into the mouse germ line via retroviral vectors; Proc. Natl. Acad. Sci.; 82:6148–6152 (1985).
Thompson, et al.; Germ line transmission and expression of a corrected HPRT gene produced by gene targeting in embryonic stem cells; Cell; 56:313–321 (1989).
C. W. Lo; Transformation by iontophoretic microinjection of DNA: Multiple integrations without tandem insertions; Molecular and Cellular Biology; 3(10):1803–1814 (1983).
Lavitrano, et al.; Sperm cells as vectors for introducing foreign DNA into eggs: Genetic transformation of mice; Cell; 57:717–723 (1989).

Gordon; Transgenic animals; Intl. Rev. Cytol; 115:171–229 (1989).
Campbell, et al.; Sheep cloned by nuclear transfer from a cultured cell line; Nature; 380(7):64–66 (1996).
I. Wilmut, et al.; Viable offspring derived from fetal and adult mammalian cells; Nature; 385:810–813 (1997).
Lakso, et al.: Targeted oncogene activation by site–specific recombination in transgenic mice; Proc. Natl. Acad. Sci.; 89:a6232–6236 (1992).
Gu, et al.; Deletion of a DNA polymerase β gene segment in T cells using cell type–specific gene targeting; Science; 265:103–106 (1994).
Kohler, et al.; Continuous cultures of fused cells secreting antibody of predefined specificity; Nature; 256:495–497 (1975).
Kozbor, et al.; The production of monoclonal antibodies from human lymphocytes; Immunology Today; 4(3):72–79 (1983).
Cote, et al.; Generation of human monoclonal antibodies reactive with cellular antigens; Proc. Natl. Acad. Sci.; 80:2026–2030 (1983).
Cole, et al.; The EBV–Hybridoma technique and its application to human lung cancer; Monoclonal Antibodies and Cancer Therapy; pp. 77–96 (1985).
Better, et al.; *Escherichia coli* secretion of an active chimeric antibody fragment; Science; 240:1041–1043 (1988).
Liu, et al.; Chimeric mouse–human IgG1 antibody that can mediate lysis of cancer cells; Proc. Natl. Acad. Sci.; 84:3439–3443 (1987).
Liu, et al.; Production of a mouse–human chimeric monoclonal antibody to CD20 with potent Fc–dependent biologic activity; The J. of Immunol.; 139:3521–3526 (1987).
Sun, et al.; Chimeric antibody with human constant regions and mouse variable regions directed against carcinoma–associated antigen 17–1A; Proc. Natl. Acad. Sci.; 84:214–218 (1987).
Nishimura, et al.; Recombinant Human–Mouse Chimeric Monoclonal Antibody Specific for Common Acute Lymphocytic Leukemia Antigen; Cancer Research; 47:999–1005 (1987).
Wood, et al.; The synthesis and in vivo assembly of functional antibodies in yeast; Nature; 314(4)446–449 (1985).
Shaw, et al.; Mouse/human chimeric antibodies to a tumor–associated antigen; biologic activity of the four human IgG subclasses; J. Natl. Cancer Inst.; 80:1553–1559 (1988).
S. L. Morrison; Transfectomas provide novel chimeric antibodies; Science; 229:1202–1207 (1985).
Oi, et al.; Chimeric antibodies; Bio/Techniques; 4:214–221 (1986).
Jones, et al.; Replacing the complementarity–determining regions in a human antibody with those from a mouse; Nature; 321:552–525 (1986).
Verhoeyen, et al.; Reshaping human antibodies: Grafting an antilysozyme activity; Science; 239:1534–1536 (1988).
Beidler, et al.; Cloning and high level expression of a chimeric antibody with specificity for human carcinoembryonic antigen; The J. of Immunology; 141:4053–4060 (1988).
Lonberg, et al.; Human antibodies from transgenic mice; Int. Rev. Immunol; 13:65–93 (1995).
Jespers, et al.; Guiding the Selection of human antibodies from phage display repertoires to a single epitope of an antigen; Bio/technology; 12:899–903 (1994).
Bird, et al.; Single–chain antigen–binding proteins; Science; 242:423–426 (1988).
Huston, et al.; Protein engineering of antibody binding sites: recovery of specific activity in an anti–digoxin single–chain Fv analogue produced in *Escherichia coli*; Proc. Natl. Acad. Sci.; 85:5879–5883 (1988).
Ward, et al.; Binding activities of a repertoire of single immunoglobulin variable domains secreted from *Escherichia coli*; Nature; 334:544–546 (1989).
Huse, et al.; Generation of a large combinatorial library of the immunoglobulin repertoire in phage lambda; Science; 246:1275–1281 (1989).
Cronin, et al.; Cystic fibrosis mutation detection by hybridization to light–generated DNA probe arrays; Human Mutation; 7:244–255 (1996).
Orita, et al.; Detection of polymorphisms of human DNA by gel electrophoresis as single–strand conformation polymorphisms; Proc. Natl. Acad. Sci.; 86:2766–2770 (1989).
M. Grompe; The rapid detection of unknown mutations in nucleic acids; Nature Genetics; 5:111–117 (1993).
Landegren, et al.; A ligase–mediated gene detection technique; Science; 241:1077–1080 (1988).
Nickerson, et al.; Automated DNA diagnostics using an ELISA–based oligonucleotide ligation assay; Proc. Natl. Acad. Sci.; 87:8923–8927 (1990).
Pastinen, et al.; Minisequencing: A specific tool for DNA analysis and diagnostics on oligonucleotide arrays; Genome Research; 7:606–614 (1997).
Pastinen, et al.; Multiplex, flourescent, solid–phase minisequencing for efficient screening of DNA sequence variation; Clinical Chemistry; 42(9):1391–1397 (1996).
Jalanko, et al.; Screening for defined cystic fibrosis mutations by solid–phase minisequencing; Clin. Chem.; 38(1):39–42 (1992).
Shumaker, et al.; Mutation detection by solid phase primer extension; Human Mutation; 7:346–354 (1996).
P. D'Eustachio, et al.; Somatic cell genetics and gene families; Science; 220:919–924 (1983).
Fan, et al.; Mapping small DNA sequences by fluorescence in situ hybridization directly on banded metaphase chromosomes; Proc. Natl. Acad. Sci.; 87:6223–6227 (1990).
Popp, et al.; A strategy for the characterization of minute chromosome rearrangements using multiple color fluorescence in situ hybridization with chromosome–specific DNA libraries and YAC clones; Hum. Genetics; 92:527–532 (1993).
Egeland, et al.; Bipolar affective disorders linked to DNA markers on chromosome 11; Nature; 325:783–787 (1987).
A. Voller, et al.; Enzyme immunoassays with special reference to ELISA techniques; J. of Clinical Pathology; 31:507–520 (1978).
J. E. Butler; The amplified ELISA: Principles of and applications for the comparative quantitation of class and subclass antibodies and the distribution of antibodies and antigens in biochemical separates; Method in Enzymology; 73:482–523 (1981).
Platt, et al.; Independent regulation of adipose tissue–specificity and obesity response of the adipsin promoter in transgenic mice; The J. of Biological Chemistry; 269(46):28558–28562 (1994).
Lam, et al.; A new type of synthetic peptide library for identifying ligand–binding activity; Nature; 354:82–84 (1991).
Houghten, et al.; Generation and use of synthetic peptide combinatorial libraries for basic research and drug discovery; Nature; 354:84–86 (1991).

Songyang, et al.; SH2 Domains recognize specific phosphopeptide sequences; Cell; 72:767–778 (1993).
Landegren et al.; A Ligase–mediated gene detection technique; Science; 241:1077–1079 (1988).
Kowoh, et al.; Transcription–based amplification system and detection of amplified human immunodeficienty virus type 1 with a bead–based sandwich hyridization format; Proc. Natl. Acad. Sci.; 86:1173–1177 (1989).
Chien, et al.; The two–hybrid system: A method to identify and clone genes for proteins that interact with a protein of interest; Proc. Natl. Acad. Sci.; 88:9578–9582 (1991).
Nakazawa, et al.; UV and skin cancer: Specific p53 gene mutation in normal skin as a biologically relevant exposure measurement; Proc. Natl. Acad. Sci.; 91:360–364 (1995).
Abravaya, et al.; Detection of point mutations with a modified ligase chain reaction (Cap–LCR); Nucleic Acids Research; 23(4):675–682 (1995).
Guatelli, et al.; Isothermal, in vitro amplification of nucleic acids by a multienzyme reaction modeled after retroviral replication; Proc. Natl. Acad. Sci.; 87:1874–1878 (1990).
Lizardi, et al.; Exponential amplification of recombinant––RNA hybridization probes; Bio/Technology; 6:1197–1202 (1988).
Kozal, et al.; Extensive polymorphisms observed in HIV–1 clade B protease gene using high–density oligonucleotide arrays; Nature Medicine: 2(7):753–759 (1996).
Maxam, et al.; A new method for sequencing DNA; Proc. Natl. Acad. Sci.; 74(2):560–564 (1977).
Sanger, et al.; DNA sequencing with chain–terminating inhibitors; Proc. Natl. Acad. Sci.; 74(12):5463–5467 (1977).
Naeve, et al.; Accuracy of automated DNA Sequencing: A multi–laboratory comparison of sequencing results; Bio/Techniques; 19(3):448–453 (1995).
Griffin, et al.; DNA sequencing; Applied Biochemistry and Biotechnology; 38:147–159 (1993).
Myers, et al.; Detection of single base substitutions by ribonuclease cleavage at mismatches in RNA: DNA duplexes; Science; 230:1242–1246 (1985).
Cotton, et al.; Reactivity of cytosine and thymine in single––base–pair mismatches with hydroxylamine and osmium tetroxide and its application to the study of mutations; Proc. Natl. Acad. Sci.; 85:4397–4401 (1988).
Saleeba, et al.; Chemical cleavage of mismatch to detect mutations; Methods in Enzymology; 217:286–295 (1992).
Hsu, et al.; Detection of DNA point mutations with DNA mismatch repair enzymes; Carcinogenesis; 15:1657–1662 (1994).
R.G.H. Cotton; Current methods of mutation detection; Mutation Research; 285:125–144 (1993).
K. Hayashi; PCR–SSCP: A method for detection of mutations; Gata; 9(3):73–79 (1992).
Keen, et al.; Rapid detection of single base mismatches as heteroduplexes on hydrolink gels; Trends Genet; 7:5.
Myers, et al.; Detection of single base substitutions in total genomic DNA; Nature; 313:495–498 (1985).
Saiki, et al.; Analysis of enzymatically amplified β–globin and HLA–DAα DNA with allele–specific oligonucleotide probes; Nature; 324:163–166 (1986).
Saiki, et al.; Genetic analysis of amplified DNA with immobilized sequence–specific oligonucleotide probes; Proc. Nalt. Acad. Sci.; 86:6230–6234 (1989).
Gibbs, et al.; Detection of single DNA base differences by competitive oligonucleotide priming; Nucleic Acid Research; 17(7):2437–2448 (1989).
J. Prosser; Detecting single–base mutations; Tibtech; 11:238–246 (1993).
Gasparini, et al.; Restriction site generating–polymerase chain reaction (RG–PCR) for the probeless detection of hidden genetic variation: application to the study of some common cystic fibrosis mutations; Molecular and Cellular Probes; 6:1:1–7 (1992).
F. Barany; Genetic disease detection and DNA amplification using cloned thermostable ligase; Proc. Natl. Acad. Sci.; 88:189–193 (1991).
Letsinger, et al.; Cholesteryl–conjugated oligonucleotides: Synthesis, properties, and activity as inhibitos of replication of human immunodeficiency virus in cell culture; Proc. Natl. Acad. Sci.; 86:6553–6556 (1989).
Lemaitre, et al.; Specific antiviral activity of a poly(L–lysine)–conjugated oligodeoxyribonucleotide sequence complementary to vesicular stomatitis virus N protein mRNA initiation site; Proc. Natl. Acad. Sci.; 84:648–652 (1987).
Krol, et al.; Modulation of Eukaryotic Gene Expression by Complementary RNA or DNA Sequences; Bio/Techniques; 6(10)958–976 (1988).
G. Zon; Oligonucleotide Analogues as Potential Chemotherapeutic Agents; Pharmaceutical Research; 5(9):539–549 (1988).
Gautier, et al.; α–DNA IV: α–anomeric and β–anomeric tetrathymidylates covalently linked to intercalating oxazolopyridocarbazole. Synthesis, physicochemical properties and poly (rA) binding; Nucleic Acids Research; 15(16):6625–6641 (1987).
Inoue, et al.; Synthesis and hybridization studies on two complementary nona(2'O–methyl)ribonucleotides; 15:6131–6148 (1987).
Inoue, et al.; Sequence–dependent hydrolysis of RNA using modified oligonucleotide splints and Rnase H; FEBS Lett.; 215(2):327–330 (1987).
Hermansson, et al.; Endothelial cell hyperplasia in human glioblastoma; Coexpresion of mRNA fo platelet–derived growth factor (PDGF) B chain and PDGF receptor suggests autocrine growth stimulation; Proc. Natl. Acad. Sci.; 85:7748–7752 (1988).
Benoist, et al.; In vivo sequence requirements of the SV40 early promoter region; Nature; 290:304–310 (1981).
Yamamoto, et al.; Identification of a functional promoter in the long terminal repeat of rous sarcoma virus; Cell; 22:787–797 (1980).
Wagner, et al.; Nucleotide sequence of the thymidine kinase gene of herpes simplex virus type 1: Proc. Natl. Acad. Sci.; 78(3):1441–1445 (1981).
Brinster, et al.; Regulation of metallothionein–thymidine kinase fusion plasmids injected into mouse eggs; Nature; 296:39–42 (1982).
Sarver, et al.; Ribozymes as potential anti–HIV–1 therapeutic agents; Science; 247:1222–1225 (1990).
J. J. Rossi; Making ribozymes work in cells; Current Biology; 4:469–471 (1994).
Haseloff, et al.; Simple RNA enzymes with new and highly specific endoribonuclease activities; Nature; 334:585–591 (1988).
Zaug, et al.; A labile phosphodiester bond at the ligation junction in a circular intervening sequence RNA; Science; 224:574–578 (1984).
Zaug, et al.; The intervening sequence RNA of tetrahymena is an enzyme; Science; 231:470–475 (1986).

Zaug, et al.; The tetrahymena ribozyme acts like an RNA restriction endonuclease; Nature; 324:429–433 (1986).
Been, et al.; One binding site determines sequence specificity of tetrahymena pre–rRNA self–splicing, trans–splicing, and RNA enzyme activity; Cell; 47:207–216 (1986).
Smithies, et al.; Insertion of DNA sequences into the human chromosomal β–globin locus by homologous recombination; Nature; 317:230–234 (1985).
Thomas, et al.; Site–directed mutagenesis by gene targeting in mouse embryo–derived stem cells; Cell; 51:503–512 (1987).
C. Helene; The anti–gene strategy: control of gene expression by triplex–forming–oligonucleotides; Anti–cancer drug design; 6:569–584 (1991).
Helene, et al.; Control of gene expression by triple helix–forming oligonucleotides; Ann. NY Acad. Sci.; 660:27–36 (1992).
L. J. Maher, III; DNA triple–helix formation: An approach to artificial gene repressors?; Bioassays; 14(12):807–815 (1992).
Linder, et al.; Pharmacogenetics: a laboratory tool for optimizing therapeutic efficiency; Clin. Chem. 43(2):254–266 (1997).
Cruikshank, et al.; A lipidated anti–tat antibody enters living cells and blocks HIV–1 viral replication; J. Acquired Immune Deficiency Syndromes and Human Retrovirology; 14:193–203 (1997).
O'Reilly, et al.; Endostain; An endogeneous inhibitor of angiogenesis and tumor growth; Cell; 88:277–285 (1997) XP000652213.
Stein, et al.; Physicochemical Properties of Phosphorotioate Oligodexynucleotides; Nucleic Acids Research; 16:3209–3221 (1988).
Griffin, et al.; The Humana Press Inc.; DNA Sequencing; 38:147–159 (1993).
Ausubel F.M., et al.; Eds.; Current Protocols in Molecular Biology; vol. 1, Green Publishing Associates Inc.
Creighton; Proteins; Structures and Molecular Principles; W.H. Freeman and Company, NY, pp. 34–49 (1983).
Sheffield, et al.; Proc. Natl. Acad. Sci.; Attachment of a 40–base–pair G + C–rich sequence (GC–clamp) to genomic DNA fragments by the polymerase chain results in improved detection of single–base changes; vol. 86, pp. 232–236 (1989).
Myers; Molecular Biology and Biotechnology: A comprehensive desk reference, VCH Publishers, New York; p. 833 (1995).
Cohen, et al.; Adv. Chromatogr.; Emerging Technologies for Sequencing Antisense Oligonucleotides: Capillary Electrophoresis and Mass Spectrometry; 36:127–162 (1996).
Maggio, E. (ed).; CC Press, Boca Ration FL; Enzyme–Immunoassay; (1980).

* cited by examiner 1 80
CCCTGGCGGGCAGATGACATCCTGGCCGGCCCCCGCGCCTGCTGGACCCCCAGCCCTACCCCGGGGCCCCGCACCACGG
81 160
CTCCTACGTGCACTTCCAGCCGGCTCGCCCCACTGGTGGGCCCGTCCACACCCACACCCACACCCACCAGGACTTCCAGC
161 240
TGGTGCTGCACCTGGTGGCCCTGAACAGCCCGCAGCCGGGCGGCATGCGAGGCATCCGGGGAGCGGACTTCCAGTGCTTC
241 320
CAGCAGGCGCGCGCCGCGGGGCTGGCCGGCACCTTCCGGGCCTTCCTGTCGTCGCGGCTGCAGGACCTCTACAGCATCGT
321 400
GCGCCGCGCCGACCGCACCGGGGTGCCCGTCGTCAACCTCAGGGACGAGGTGCTCTTCCCCAGCTGGGAGGCCTTATTCT
401 480
CGGGCTCCGAGGGCCAGCTGAAGCCCGGGGCCCGCATCTTCTCTTTCGACGGCAGAGATGTCCTGCAGCACCCCGCCTGG
481 560
CCCCGGAAGAGCGTGTGGCACGGCTCCGACCCCAGCGGGCGCCGCCTGACCGACAGCTACTGCGAGACGTGGCGGACGGA
561 640
GGCCCCGGCGGCCACCGGGCAGGCGTCGTCGCTGCTGGCGGGCAGGCTGCTGGAGCAGGAGGCCGCGAGCTGCCGCCACG
641 720
CCTTCGTGGTGCTCTGCATCGAGAACAGCGTCATGACCTCCTTCTCCAAGTAGGGCCGCGCGGCCCACGGACAGGCGGGG
721 800
GAGGGGGCGCCCGCAGGAGCATCCGCCGCCCCGGGGGGGCCTGGCCGGGACGCTTGCCTGCACCGTCACGTTTAATGTAA
801 829
TCCTCAAGAAATAAAAGGAAGCCAAAGAG

FIG. 2

1 ccctggcgggcagatgacatcctggccggcccccgcgcctgctg
P W R A D D I L A G P P R L L 15
46 gacccccagccctaccccggggccccgcaccacggctcctacgtg
D P Q P Y P G A P H H G S Y V 30
91 cacttccagccggctcgccccactggtgggcccgtccacacccac
H F Q P A R P T G G P V H T H 45
136 acccacacccaccaggacttccagctggtgctgcacctggtggcc
T H T H Q D F Q L V L H L V A 60
181 ctgaacagcccgcagccgggcggcatgcgaggcatccggggagcg
L N S P Q P G G M R G I R G A 75
226 gacttccagtgcttccagcaggcgcgcgccgcggggctggccggc
D F Q C F Q Q A R A A G L A G 90
271 accttccgggccttcctgtcgtcgcggctgcaggacctctacagc
T F R A F L S S R L Q D L Y S 105
316 atcgtgcgccgcgccgaccgcaccggggtgcccgtcgtcaacctc
I V R R A D R T G V P V V N L 120
361 agggacgaggtgctcttccccagctgggaggccttattctcgggc
R D E V L F P S W E A L F S G 135
406 tccgagggccagctgaagcccggggcccgcatcttctctttcgac
S E G Q L K P G A R I F S F D 150
451 ggcagagatgtcctgcagcaccccgcctggccccggaagagcgtg
G R D V L Q H P A W P R K S V 165
496 tggcacggctccgaccccagcgggcgccgcctgaccgacagctac
W H G S D P S G R R L T D S Y 180
541 tgcgagacgtggcggacggaggccccggcggccaccgggcaggcg
C E T W R T E A P A A T G Q A 195
586 tcgtcgctgctggcgggcaggctgctggagcaggaggccgcgagc
S S L L A G R L L E Q E A A S 210
631 tgccgccacgccttcgtggtgctctgcatcgagaacagcgtcatg
C R H A F V V L C I E N S V M 225
676 acctccttctccaagtagggccgcgcggcccacggacaggcgggg
T S F S K * 230
721 gaggggcgcccgcaggagcatccgccgccccggggggcctggc
766 cgggacgcttgcctgcaccgtcacgtttaatgtaatcctcaagaa
811 ataaaaggaagccaaagag

FIG. 3

1 80
CACACCCACCAGGACTTCCAGCTGGTGCTGCACCTGGTGGCCCTGAACAGCCCGCAGCCGGGCGGCATGCGAGGCATCCG
81 160
GGGAGCGGACTTCCAGTGCTTCCAGCAGGCGCGCCGCGGGGCTGGCCGGCACCTTCCGGGCCTTCCTGTCGTCGCGGC
161 240
TGCAGGACCTCTACAGCATCGTGCGCCGCGCCGACCGCACCGGGGTGCCCGTCGTCAACCTCAGGGACGAGGTGCTCTTC
241 320
CCCAGCTGGGAGGCCTTATTCTCGGGCTCCGAGGGCCAGCTGAAGCCCGGGGCCCGCATCTTCTCTTTCGACGGCAGAGA
321 400
TGTCCTGCAGCACCCCGCCTGGCCCCGGAAGAGCGTGTGGCACGGCTCCGACCCCAGCGGGCGCCGCCTGACCGACAGCT
401 480
ACTGCGAGACGTGGCGGACGGAGGCCCCGGCGGCCACCGGGCAGGCGTCGTCGCTGCTGGCGGGCAGGCTGCTGGAGCAG
481 555
GAGGCCGCGAGCTGCCGCCACGCCTTCGTGGTGCTCTGCATCGAGAACAGCGTCATGACCTCCTTCTCCAAGTAG

FIG. 4

```
  1 cacacccaccaggacttccagctggtgctgcacctggtggccctg
    H  T  H  Q  D  F  Q  L  V  L  H  L  V  A  L     15
 46 aacagcccgcagccgggcggcatgcgaggcatccggggagcggac
    N  S  P  Q  P  G  G  M  R  G  I  R  G  A  D     30
 91 ttccagtgcttccagcaggcgcgcgccgcggggctggccggcacc
    F  Q  C  F  Q  Q  A  R  A  A  G  L  A  G  T     45
136 ttccgggccttcctgtcgtcgcggctgcaggacctctacagcatc
    F  R  A  F  L  S  S  R  L  Q  D  L  Y  S  I     60
181 gtgcgccgcgccgaccgcaccggggtgcccgtcgtcaacctcagg
    V  R  R  A  D  R  T  G  V  P  V  V  N  L  R     75
226 gacgaggtgctcttccccagctgggaggccttattctcgggctcc
    D  E  V  L  F  P  S  W  E  A  L  F  S  G  S     90
271 gagggccagctgaagcccggggcccgcatcttctctttcgacggc
    E  G  Q  L  K  P  G  A  R  I  F  S  F  D  G     105
316 agagatgtcctgcagcaccccgcctggccccggaagagcgtgtgg
    R  D  V  L  Q  H  P  A  W  P  R  K  S  V  W     120
361 cacggctccgaccccagcgggcgccgcctgaccgacagtactgc
    H  G  S  D  P  S  G  R  R  L  T  D  S  Y  C     135
406 gagacgtggcggacggaggccccggcggccaccgggcaggcgtcg
    E  T  W  R  T  E  A  P  A  A  T  G  Q  A  S     150
451 tcgctgctggcgggcaggctgctggagcaggaggccgcgagctgc
    S  L  L  A  G  R  L  L  E  Q  E  A  A  S  C     165
496 cgccacgccttcgtggtgctctgcatcgagaacagcgtcatgacc
    R  H  A  F  V  V  L  C  I  E  N  S  V  M  T     180
541 tccttctccaagtag
    S  F  S  K  *                                   184
```

FIG. 5

| | | |
|---|---|---|
| 1 | HTHQDFQLVLHLVALNSPQFGGMRGIRGADFQCFQQARAAGLAGTFRAFLSSRLQDLYSI | endostatin-canine.PRO |
| 1 | HVHQDFQPALHLVALNIPLSGGMRGIRGADFQCFQQARQVGLAGTFRAFLSSRLQDLYSI | endostatin-chicken.PRO |
| 1 | HSHRDFQPVLHLVALNSPLSGGMRGIRGADFQCFQQARAVGLAGTFRAFLSSRLQDLYSI | endostatin-human.PRO |
| 1 | HTHQDFQPVLHLVALNIPLSGGMRGIRGADFQCFQQARAVGLSGTFRAFLSSRLQDLYSI | endostatin-mouse.PRO |
| 61 | VRRADRTGVPVVNLRDEVLFPSWEALFSGSEGQLKPGARIFSFDGRDVLQHPAWPRKSVW | endostatin-canine.PRO |
| 61 | VRRADRTAVPIVNLRDEVLFSNWEALFTGSEAPLRAGARILSFDGRDILQDSAWPQKSIW | endostatin-chicken.PRO |
| 61 | VRRADRAAVPIVNLKDELLFPSWEALFSGSEGPLKPGARIFSFDGKDVLRHPIWPQKSVW | endostatin-human.PRO |
| 61 | VRRADRGSVPIVNLKDEVLSPSWDSLFSGSQGQLQPGARIFSFDGRDVLRHPAWPQKSVW | endostatin-mouse.PRO |
| 121 | HGSDPSGRRLTDSYCETWRTEAPAATGQASSLLAGRLLEQEAASCRHAFVVLCIENSVMT | endostatin-canine.PRO |
| 121 | HGSDAKGRRLFESYCEAWRTDERGTSGQASSLSSGKLLEQSASSCQHAFVVLCIENSFMT | endostatin-chicken.PRO |
| 121 | HGSDPNGRRLTESYCETWRTEAPSATGQASSLLGGRLLGQSAASCHHAYIVLCIENSFMT | endostatin-human.PRO |
| 121 | HGSDPSGRRLMESYCETWRTETTGATGQASSLLSGRLLEQKAASCHNSYIVLCIENSFMT | endostatin-mouse.PRO |
| 181 | SFSK | endostatin-canine.PRO |
| 181 | AAKK | endostatin-chicken.PRO |
| 181 | ASK | endostatin-human.PRO |
| 181 | SFSK | endostatin-mouse.PRO |

FIG. 6

METHODS AND COMPOSITIONS FOR DIAGNOSING AND TREATING DISORDERS INVOLVING ANGIOGENESIS

CROSS REFERENCE TO RELATED APPLICATIONS

This application claims the benefit of priority from United States Provisional Application No. 60/227,924, filed Aug. 25, 2000.

The present invention relates to polynucleotide sequences which are shown herein to be associated with the regulation of angiogenesis. More specifically, the present invention relates to novel polynucleotide sequences which encode the angiogenesis inhibitor endostatin, and more particularly, the canine angiogenesis inhibitor. The invention encompasses endostatin nucleic acids, recombinant DNA molecules, cloned genes and degenerate variants thereof, vectors containing such endostatin nucleic acids, and hosts that have been genetically engineered to express and/or contain such molecules. The invention further relates to endostatin gene products and antibodies directed against such gene products. The invention further relates to methods for the identification of compounds that modulate the expression, synthesis and activity of such endostatin nucleic acids, and to methods of using compounds such as those identified herein as therapeutic agents in the treatment of angiogenesis-related disorders, including, but not limited to, cancer. The invention also relates to methods for the diagnostic evaluation, genetic testing and prognosis of an angiogenesis-related disorder, including, but not limited to, cancer.

BACKGROUND OF THE INVENTION

Angiogenesis, defined as the growth or sprouting of new blood vessels from existing vessels, is a complex process that primarily occurs during embryonic development. Under normal physiological conditions in adults, angiogenesis takes place only in very restricted situations such as hair growth and wounding healing (Auerbach, W. and Auerbach, R., 1994, *Pharmacol Ther* 63(3):265-3 11; Ribatti et al., 1991, *Haematologica* 76(4):3 11-20; Risau, 1997, *Nature* 386(6626):67 1-4). Unregulated angiogenesis has gradually been recognized to be responsible for a wide range of disorders, including, but not limited to, cancer, cardiovascular disease, rheumatoid arthritis, psoriasis and diabetic retinopathy (Folkman, 1995, *Nat Med* 1(1):27–31; Isner, 1999, *Circulation* 99(13): 1653–5; Koch, 1998, *Arthritis Rheum* 41(6):951–62; Walsh, 1999, *Rheumatology* (*Oxford*) 38(2):103–12; Ware and Simons, 1997, *Nat Med* 3(2): 158–64). Of particular interest is the observation that angiogenesis is required by solid tumors for their growth and metastases (Folkman, 1986, Cancer Res, 46(2) 467–73. Folkman 1990, J Natl. Cancer Inst., 82(1) 4–6, Folkman, 1992, *Semin Cancer Biol* 3(2):65–71; Zetter, 1998, *Annu Rev Med* 49:407–24). A tumor usually begins as a single aberrant cell which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. The precise mechanisms that control the angiogenic switch is not well understood, but it is believed that neovascularization of tumor mass results from the net balance of a multitude of angiogenesis stimulators and inhibitors (Folkman, 1995, *Nat Med* 1(1):27–31).

One of the most potent angiogenesis inhibitors is endostatin identified by O'Reilly and Folkman (O'Reilly et al., 1997, *Cell* 88(2):277–85; O'Reilly et al., 1994, Cell 79(2):3 15–28). Its discovery was based on the phenomenon that certain primary tumors can inhibit the growth of distant metastases. O'Reilly and Folkman hypothesized that a primary tumor initiates angiogenesis by generating angiogenic stimulators in excess of inhibitors. However, angiogenic inhibitors, by virtue of their longer half life in the circulation, reach the site of a secondary tumor in excess of the stimulators. The net result is the growth of primary tumor and inhibition of secondary tumor. Endostatin is one of a growing list of such angiogenesis inhibitors produced by primary tumors. It is a proteolytic fragment of a larger protein: endostatin is a 20 kDa fragment of collagen XVIII (amino acid H1132-K1315 in murine collagen XVIII). Endostatin has been shown to specifically inhibit endothelial cell proliferation in vitro and block angiogenesis in vivo. More importantly, administration of endostatin to tumor-bearing mice leads to significant tumor regression, and no toxicity or drug resistance has been observed even after multiple treatment cycles (Boehm et al., 1997, *Nature* 390 (6658):404–407). The fact that endostatin targets genetically stable endothelial cells and inhibits a variety of solid tumors makes it a very attractive candidate for anticancer therapy (Fidler and Ellis, 1994, *Cell* 79(2):185–8; Gastl et al., 1997, *Oncology* 54(3):177–84; Hinsbergh et al., 1999, *Ann Oncol* 10 Suppl 4:60–3). In addition, angiogenesis inhibitors have been shown to be more effective when combined with radiation and chemotherapeutic agents (Klement, 2000, J. Clin Invest, 105(8) R15–24. Browder, 2000, Cancer Res. 6-(7) 1878–86, Arap et al., 1998, *Science* 279(5349) :377–80; Mauceri et al., 1998, *Nature* 394(6690):287–91).

Cancer is not only devastating to humans, but is also the most common cause of natural death in dogs. (Bronson, 1982, Am J Vet Res, 43(11) 2057–9). Dogs develop tumors twice as frequently as humans and it has been reported that 45–50% of dogs that live to 10 years or older die of cancer; regardless of age, and that 23% of dogs that present for necropsy died of cancer(Bronson, 1982, Am J Vet Res, 43(11) 2057–9). Surgical removal of the tumor is the most common treatment, but the prognosis for invasive/metastatic tumor is very poor, with median survival time ranging from weeks to months. Other treatments, such as radiation therapy and chemotherapy, have only very limited success (Bostock, 1986, Br Vet J 142(6):506–15; Bostock, 1986, Br Vet J 142(1):1–19; MacEwen, 1990, *Cancer Metastasis Rev* 9(2): 125–36). Thus, more effective treatments for angiogenic diseases, such as, for example, canine cancers, are necessary.

SUMMARY OF THE INVENTION

The present invention encompasses novel nucleotide sequences that are associated with angiogenesis related disorders, e.g., cancer. The invention more specifically relates to nucleotide sequences that encode endostatin. In addition, endostatin nucleic acids, recombinant DNA molecules, cloned genes or degenerate variants thereof are provided herein. The invention also provides vectors, including expression vectors, containing endostatin nucleic acid molecules, and hosts that have been genetically engineered to express and/or contain such endostatin gene products.

The invention further relates to novel endostatin gene products and to antibodies directed against such gene products, or variants or fragments thereof.

The invention further relates to methods for modulation of endostatin-mediated processes and for the treatment of disorders involving angiogenesis, such as cancer, including the amelioration or prevention of at least one symptom of the disorders, wherein such methods comprise administering a compound which modulates the expression of an endostatin gene and/or the synthesis or activity of an endostatin gene product. In one embodiment, the invention relates to methods for the use of a novel endostatin gene product or fragment, analog, or mimetic thereof, or an antibody or antibody fragment directed against an endostatin gene product, to treat or ameliorate a symptom of such disorders.

Such disorders include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; wound granulation; corornary collaterals; cerebral collaterals; arteriovenous malformations; ischemic limb angiogenesis; diabetic neovascularization; macular degeneration; fractures; vasculogenesis; hematopoiesis; ovulation; menstruation; and placentation.

The invention further relates to methods for modulation of endostatin-mediated processes and for the treatment of disorders involving abnormal stimulation of endothelial cells, including the amelioration or prevention of at least one symptom of the disorders, wherein such methods comprise administering a compound which modulates the expression of an endostatin gene and/or the synthesis or activity of an endostatin gene product. In one embodiment, the invention relates to methods for the use of a novel endostatin gene product or fragment, analog, or mimetic thereof, or an antibody or antibody fragment directed against an endostatin gene product, to treat or ameliorate a symptom of such disorders.

The endothelial cell proliferation inhibiting proteins of the present invention are useful in the treatment of disease of excessive or abnormal stimulation of endothelial cells. These diseases include, but are not limited to, intestinal adhesions, atherosclerosis, scleroderma, and hypertrophic scars, i.e., keloids. They are also useful in the treatment of diseases that have angiogenesis as a pathologic consequence such as cat scratch disease (Rochele minalia quintosa) and ulcers (Helobacter pylori).

The invention further relates to methods for blocking interactions between endostatin and its respective receptors with analogs that act as receptor antagonists. These antagonists may promote endothelialization and vascularization. Such effects may be desirable in situations including, but not limited to, inadequate vascularization of the uterine endometrium and associated infertilty, wound repair, healing of cuts and incisions, treatment of vascular problems in diabetics, especially retinal and peripheral vessels, promotion of vascularization in transplanted tissue including muscle and skin, promotion of vascularization of cardiac muscle especially following transplantation of a heart or heart tissue and after bypass surgery, promotion of vascularization of solid and relatively avascular tumors for enhanced cytotoxin delivery, and enhancement of blood flow to the nervous system, including but not limited to the cerebral cortex and spinal cord.

The term "endostatin-related disorder" as used herein, refers to disorders involving an endostatin gene or gene product, or an aberrant level of endostatin gene expression, gene product synthesis and/or gene product activity, respectively, relative to levels found in normal, unaffected, unimpaired individuals, levels found in clinically normal individuals, and/or levels found in a population whose levels represent baseline, average endostatin levels.

The term "endostatin-mediated process" as used herein, includes processes dependent and/or responsive, either directly or indirectly, to the level of expression, gene product synthesis and/or gene product activity of endostatin genes.

In another embodiment, such methods can comprise modulating the level of expression or the activity of an endostatin gene product in a cell such that the endostatin-mediated process or the disorder is treated, e.g., a symptom is ameliorated. In another embodiment, such methods can comprise supplying a nucleic acid molecule encoding an endostatin gene product to increase the level, expression or activity of the endostatin gene product within the cell such that the endostatin-mediated process or the disorder is treated, e.g., a symptom is ameliorated. The nucleic acid molecule encoding the endostatin gene product can encode a mutant endostatin gene product with increased activity or expression levels.

The invention still further relates to methods for modulation of endostatin-mediated processes or the treatment of endostatin-related disorders, such as cancer, including, but not limited to, disorders resulting from endostatin gene mutations, and/or an abnormal levels of endostatin expression or activity and disorders involving one or more endostatin genes or gene products, wherein treatment includes the amelioration or prevention of at least one symptom of such disorders. In one embodiment, such methods can comprise supplying a mammal in need of treatment with a nucleic acid molecule encoding an unimpaired endostatin gene product such that the unimpaired endostatin gene product is expressed and the disorder is treated, e.g., a symptom is ameliorated. In another embodiment, such methods can comprise supplying a mammal in need of treatment with a cell comprising a nucleic acid molecule that encodes an unimpaired endostatin gene product such that the cell expresses the unimpaired endostatin gene product and the disorder is treated, e.g., a symptom is ameliorated. In yet another embodiment, such methods comprise supplying a mammal in need of treatment with a modulatory compound, such as, for example, a small molecule, peptide or antibody that is capable of modulating the activity of an endostatin gene or gene product.

In addition, the present invention is directed to methods that utilize endostatin gene sequences and/or endostatin gene product sequences for the diagnostic evaluation, genetic testing and/or prognosis of angiogenesis-related disorders, such as cancer. For example, the invention relates to methods for diagnosing angiogenesis-related disorders, e.g., cancer, wherein such methods can comprise measuring endostatin gene expression in a patient sample, or detecting an endostatin mutation that correlates with the presence or development of such a disorder, in the genome of a mammal suspected of exhibiting such a disorder.

The present invention also is directed to utilizing the endostatin gene sequences and/or gene products as markers for mapping of the human chromosome.

The invention still further relates to methods for identifying compounds capable of modulating the expression of an endostatin gene and/or the synthesis or activity of an endostatin gene product, wherein such methods comprise contacting a compound with a cell that expresses such an endostatin gene, measuring the levels of endostatin gene expression, gene product expression or gene product activity, and comparing such levels to the levels of endostatin gene expression, gene product, or gene product activity produced by the cell in the absence of such compound, such that if the level obtained in the presence of the compound differs from that obtained in its absence, a compound capable of modulating the expression of the endostatin gene and/or the synthesis or activity of the endostatin gene product has been identified.

DEFINITIONS

As used herein, the following terms shall have the abbreviations indicated.

| | |
|---|---|
| BAC: | bacterial artificial chromosome |
| bp: | base pair(s) |
| dbEST: | expressed sequence tag data base (National Center for Biotechnology Information) |
| EST: | expressed sequence tag |
| RT-PCR: | reverse transcriptase PCR |
| SSCP: | single-stranded conformational polymorphism |
| SNP: | single nucleotide polymorphism |
| YAC: | yeast artificial chromosome |

BRIEF DESCRIPTION OF THE FIGURES

FIG. 1 shows results of an amplification reaction of dog liver RNA. A region of canine collagen XVIII which contains endostatin (proendo) were specifically amplified. The positions of PCR products of expected size are indicated by an arrow.

FIG. 2: The nucleotide sequence of canine pro-endostatin (SEQ ID NO: 1).

FIG. 3: The amino acid sequence of canine pro-endostatin translated from the sequence of FIG. 2 (SEQ ID NO:2). The region corresponding to endostatin is in bold (amino acid residues 47–230). The stop codon is indicated by *.

FIG. 4: The nucleotide sequence of canine endostatin (SEQ ID NO:3).

FIG. 5: The amino acid sequence of canine endostatin translated from the sequence of FIG. 4 (SEQ ID NO:4). The stop codon is indicated by *.

FIG. 6: An amino acid alignment of endostatin from canine, chicken, human and mouse. The program used is Lasergene MegAlign, aligned by Clustal method (DNA Star Inc., Madision, Wis.).

DETAILED DESCRIPTION OF THE INVENTION

Figure 1:
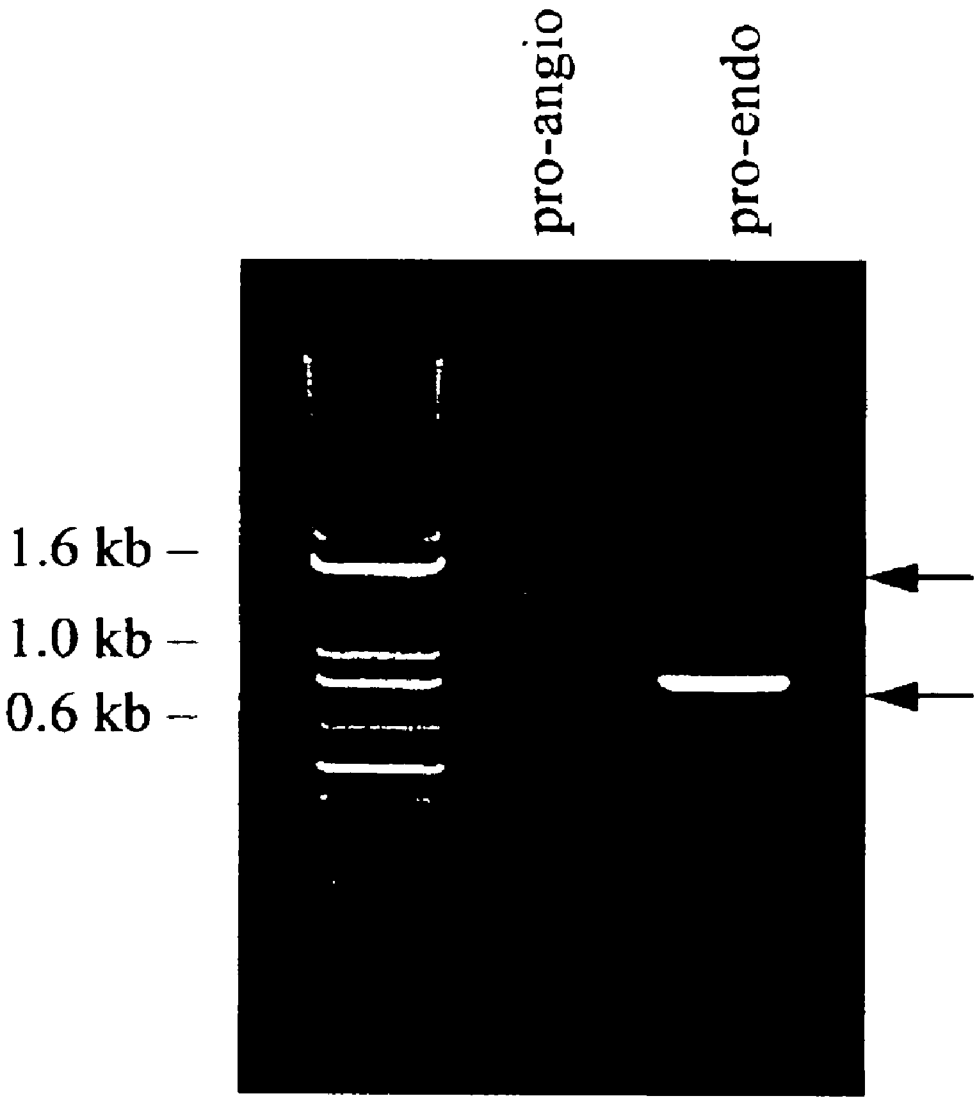
FIG. 1: RT-PCR analysis of dog liver RNA.

Compositions and methods relating to nucleic acid sequences associated with disorders involving angiogenesis are described herein. Novel genes which are associated with angiogenesis-related disorders have been identified. Such genes encode endostatin. In particular, described below are endostatin nucleic acid molecules, as well as vectors comprising these molecules, host cells engineered to contain and/or express such molecules, endostatin gene products, and antibodies that specifically recognize such gene products. Also described are various uses of these nucleic acids, polypeptides, and antibodies, as well as methods for their detection. For example, methods for the use of these molecules for modulation of angiogenesis-related processes and for treatment of angiogenesis-related disorders, such as cancer, are described. Screening assays for compounds that interact with an endostatin gene or gene product, or modulate endostatin gene or gene product activity also are described below. Methods of treatment of an angiogenesis-related disorder using the compositions of the invention and compositions identified by the methods of the invention are further described. Finally, pharmaceutical compositions for use with the compositions of the invention are described.

Endostatin nucleic acid molecules are described in this section. Unless otherwise stated, the term "endostatin nucleic acid" refers collectively to the sequences described herein.

The endostatin nucleic acid molecules of the invention include:

(a) a nucleic acid molecule containing the DNA sequence of endostatin (FIG. 4 (SEQ ID NO:3)) and fragments thereof;

(b) a nucleic acid molecule comprising an endostatin nucleic acid sequence (e.g., the nucleic acid sequences depicted in FIG. 2 (SEQ ID NO:1)) or a fragment thereof;

(c) a nucleic acid molecule that encodes an endostatin gene product;

(d) a nucleic acid molecule that comprises at least one exon of an endostatin gene;

(e) a nucleic acid molecule that comprises endostatin gene sequences of upstream untranslated regions, intronic regions, and/or downstream untranslated regions, or fragments thereof, of the endostatin nucleotide sequences in (b) above;

(f) a nucleic acid molecule comprising the novel endostatin sequences disclosed herein that encodes mutants of the endostatin gene products in which all or a part of one or more of the domains is deleted or altered, as well as fragments thereof;

(g) nucleic acid molecules that encode fusion proteins comprising an endostatin gene product, or a fragment thereof, fused to a heterologous polypeptide;

(h) nucleic acid molecules within the endostatin genes described in b), above (e.g., primers), or within chromosomal nucleotide sequences flanking the endostatin gene, which can be utilized as part of the methods of the invention for identifying and diagnosing individuals at risk for, or exhibiting an angiogenesis-related disorder, such as cancer, or can be used for mapping human chromosomes; and;

(i) nucleic acid molecules within the endostatin genes described in b), above, or within chromosomal nucleotide sequences flanking the endostatin genes, which correlate with an angiogenesis-related disorder, such as cancer.

The endostatin nucleotide sequences of the invention further include nucleotide sequences corresponding to the nucleotide sequences of (a)–(i) above wherein one or more of the exons, or fragments thereof, have been deleted.

The endostatin nucleotide sequences of the invention also include nucleotide sequences greater than 20, 30, 40, 50, 60, 70, 80, 90, 100, or more base pairs long that have at least 85%, 90%, 95%, 98%, or more nucleotide sequence identity to the endostatin nucleotide sequences of (a)–(i) above, with the proviso that the endostatin is not chicken, human, or mouse endostatin.

The endostatin nucleotide sequences of the invention further include nucleotide sequences that encode polypeptides having at least 85%, 90%, 95%, 98%, or higher amino acid sequence identity to the polypeptides encoded by the endostatin nucleotide sequences of (a)–(i) above.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical overlapping positions/total # of overlapping positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264–2268, modified as in Karlin and Altschul, 1993, Proc. Natl. Acad. Sci. USA 90:5873–5877. Such an algorithm is incorporated into the NBLAST and XBLAST programs of Altschul, et al., 1990, J. Mol. Biol. 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al., 1997, *Nucleic Acids Res.*25:3389–3402. Alternatively, PSI-Blast can be used to perform an iterated search which detects distant relationships between molecules (Altschul et al., 1997, supra). When utilizing BLAST, Gapped BLAST, and PSI-Blast programs, the default parameters of the respective programs (e.g., XBLAST and NBLAST) can be used (see http://www.ncbi.nlm.nih.gov). Another preferred, non-limiting example of a mathematical algorithm utilized for the comparison of two sequences is the algorithm of Karlin and Altschul, 1990, Proc. Natl. Acad. Sci. USA 87:2264–2268, modified as in Karlin and Altschul, 1993, Proc. Natl. Acad. Sci. USA 90:5873–5877. Such an algorithm is incorporated into the NBLAST and XBLAST programs of Altschul, et al., 1990, J. Mol. Biol. 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al., 1997, *Nucleic Acids Res.*25:3389–3402. Alternatively, PSI-Blast can be used to perform an iterated search which detects distant relationships between molecules (Altschul et al., 1997, supra). When utilizing BLAST, Gapped BLAST, and PSI-Blast programs, the default parameters of the respective programs (e.g., XBLAST and NBLAST) can be used (see http://www.ncbi.nlm.nih.gov). Another preferred, non-limiting example of a mathematical algorithm utilized for the comparison of sequences is the algorithm of Myers and Miller, 1988, CABIOS 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

The endostatin nucleotide sequences of the invention further include: (a) any nucleotide sequence that hybridizes to an endostatin nucleic acid molecule of the invention under stringent conditions, e.g., hybridization to filter-bound DNA in 6×sodium chloride/sodium citrate (SSC) at about 45° C. followed by one or more washes in 0.2×SSC/0.1% SDS at about 50–65° C., or (b) under highly stringent conditions, e.g., hybridization to filter-bound nucleic acid in 6×SSC at about 45° C. followed by one or more washes in 0.1×SSC/0.2% SDS at about 68° C., or under other hybridization conditions which are apparent to those of skill in the art (see, for example, Ausubel F. M. et al., eds., 1989, Current Protocols in Molecular Biology, Vol. I, Green Publishing Associates, Inc., and John Wiley & sons, Inc., New York, at pp. 6.3.1–6.3.6 and 2.10.3). Preferably the endostatin nucleic acid molecule that hybridizes under conditions described under (a) and (b), above, is one that comprises the complement of a nucleic acid molecule that encodes an endostatin gene product. In a preferred embodiment, nucleic acid molecules that hybridize under conditions (a) and (b), above, encode gene products, e.g., gene products functionally equivalent to an endostatin gene product.

Functionally equivalent endostatin gene products include naturally occurring endostatin gene products present in the same or different species. Functionally equivalent endostatin gene products also include gene products that retain at least one of the biological activities of an endostatin gene product, and/or which are recognized by and bind to antibodies (polyclonal or monoclonal) directed against such gene product.

Among the nucleic acid molecules of the invention are deoxyoligonucleotides ("oligos") which hybridize under highly stringent or stringent conditions to the endostatin nucleic acid molecules described above. In general, for probes between 14 and 70 nucleotides in length the melting temperature (Tm) is calculated using the formula: Tm(° C.)=81.5+16.6 (log [monovalent cations (molar)])+0.41 (% G+C)-(500/N) where N is the length of the probe. If the hybridization is carried out in a solution containing formamide, the melting temperature is calculated using the equation Tm(° C.)=81.5+16.6 (log[monovalent cations (molar)])+0.41(% G+C)-(0.61% formamide)-(500/N) where N is the length of the probe. In general, hybridization is carried out at about 20–25 degrees below Tm (for DNA—DNA hybrids) or 10–15 degrees below Tm (for RNA-DNA hybrids).

Exemplary highly stringent conditions may refer, e.g., to washing in 6×SSC/0.05% sodium pyrophosphate at 37° C. (for about 14-base oligos), 48° C. (for about 17-base oligos), 55° C. (for about 20-base oligos), and 60° C. (for about 23-base oligos).

The nucleic acid molecules of the invention further comprise the complements of the nucleic acids described above. Such molecules can, for example, act as antisense molecules, useful, for example, in endostatin gene regulation, and/or as antisense primers in amplification reactions of endostatin gene nucleic acid sequences.

The nucleic acid sequences of the invention may be used as part of ribozyme and/or triple helix sequences, also useful for endostatin gene regulation. Still further, such molecules may be used as components of diagnostic methods whereby, for example, the presence of a particular endostatin allele involved in an angiogenesis-related disorder, e.g., cancer, may be detected, or whereby the methods involve mapping the human chromosomal region spanned by the alleles.

Fragments of the endostatin nucleic acid molecules refer to endostatin nucleic acid sequences that can be at least 10, 12, 15, 20, 30, 40, 50, 60, 70, 80, 90, 100, 200, 300, 400, 500, 600, 700, 800, 900, 1000, 1250, 1500, 1750, 2000, 2250, 2500, 2750, 3000, 3250, 3500, 3750, 4000, 4250, 4500, 4750, 5000, or more contiguous nucleotides in length. Alternatively, the fragments can comprise sequences that encode at least 10, 20, 30, 40, 50, 100, 150, 200, 250, 300, 350, 400, 450 or more contiguous amino acid residues of the endostatin gene products. In one embodiment, the endostatin nucleic acid molecules encode a gene product exhibiting at least one biological activity of a corresponding endostatin gene product, e.g., an endostatin gene product. Fragments of the endostatin nucleic acid molecules can refer also to endostatin exons or introns, and, further, can refer to portions of endostatin coding regions that encode domains of endostatin gene products.

With respect to identification and isolation of endostatin nucleotide sequences, such sequences can be readily obtained, for example, by utilizing standard sequencing and bacterial artificial chromosome (BAC) technologies.

As will be appreciated by those skilled in the art, DNA sequence polymorphisms of an endostatin gene will exist within a population of individual organisms (e.g., within a human or canine population). Such polymorphisms may exist, for example, among individual organisms within a population due to natural allelic variation. Such polymorphisms include ones that lead to changes in amino acid sequence. As used herein, the phrase "allelic variant" refers to a nucleotide sequence which occurs at a given locus or to a gene product encoded by that nucleotide sequence. Such natural allelic variations can result in 1–5%, 5–20%, or 20–50% variance in the nucleotide sequence of a given gene. An allele is one of a group of genes which occur alternatively at a given genetic locus. Alternative alleles can be identified by sequencing the gene of interest in a number of different individual organisms. This can be readily carried out by using hybridization probes to identify the same genetic locus in a variety of individual organisms. As used herein, the terms "gene" and "recombinant gene" refer to nucleic acid molecules comprising an open reading frame encoding a polypeptide of the invention. The term can further include nucleic acid molecules comprising upstream and/or exon/intron sequences and structure.

With respect to the cloning of additional allelic variants of the human endostatin gene and homologs and orthologs from other species (e.g., guinea pig, cow, mouse, canine), the isolated endostatin gene sequences disclosed herein may be labeled and used to screen a cDNA library constructed from mRNA obtained from appropriate cells or tissues (e.g., liver) derived from the organism (e.g., guinea pig, cow, mouse, canine) of interest. The hybridization conditions used should generally be of a lower stringency when the cDNA library is derived from an organism different from the type of organism from which the labeled sequence was derived, and can routinely be determined based on, e.g., relative relatedness of the target and reference organisms.

Alternatively, the labeled fragment may be used to screen a genomic library derived from the organism of interest, again, using appropriately stringent conditions. Appropriate stringency conditions are well known to those of skill in the art as discussed above, and will vary predictably depending on the specific organisms from which the library and the labeled sequences are derived. For guidance regarding such conditions see, for example, Sambrook, et al., 1989, Molecular Cloning, A Laboratory Manual, Second Edition, Cold Spring Harbor Press, New York; and Ausubel, et al., 1989–1999, Current Protocols in Molecular Biology, Green Publishing Associates and Wiley Interscience, New York, both of which are incorporated herein by reference in their entirety.

Further, an endostatin gene allelic variant may be isolated from, for example, human or canine nucleic acid, by performing PCR using two degenerate oligonucleotide primer pools designed on the basis of amino acid sequences within the endostatin gene products disclosed herein. The template for the reaction may be cDNA obtained by reverse transcription of mRNA prepared from, for example, human or non-human cell lines or tissue known or suspected to express a wild type or mutant endostatin gene allele (such as, for example, liver cells). In one embodiment, the allelic variant is isolated from an individual organism that has an angiogenesis-mediated disorder.

The PCR product may be subcloned and sequenced to ensure that the amplified sequences represent the sequences of an endostatin gene nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to isolate genomic clones via the screening of a genomic library.

PCR technology also may be utilized to isolate full length cDNA sequences, as well as cDNA sequences corresponding to alternatively spliced mRNA species. For example, RNA may be isolated, following standard procedures, from an appropriate cellular or tissue source (i.e., one known, or suspected, to express the endostatin gene, such as, for example, liver tissue samples obtained through biopsy or post-mortem). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNase H, and second strand synthesis may then be primed with a poly-C primer. Thus, cDNA sequences upstream of the amplified fragment may easily be isolated. For a review of cloning strategies that may be used, see e.g., Sambrook et al., 1989, supra, or Ausubel et al., supra.

A cDNA of an allelic, e.g., mutant, variant of the endostatin gene may be isolated, for example, by using PCR, a technique that is well known to those of skill in the art. In this case, the first cDNA strand may be synthesized by hybridizing an oligo-dT oligonucleotide to mRNA isolated from tissue known or suspected to be expressed in an individual organism putatively carrying a mutant endostatin allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant endostatin allele to that of the normal endostatin allele, the mutation(s) responsible for the loss or alteration of function of the mutant endostatin gene product can be ascertained.

Alternatively, a genomic library can be constructed using DNA obtained from an individual organism suspected of or known to carry a mutant endostatin allele, or a cDNA library can be constructed using RNA from a tissue known, or suspected, to express a mutant endostatin allele. An unimpaired endostatin gene, or any suitable fragment thereof, may then be labeled and used as a probe to identify the corresponding mutant endostatin allele in such libraries. Clones containing the mutant endostatin gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant endostatin allele in an individual organism suspected of or known to carry such a mutant allele. In this manner, gene products made by the putatively mutant tissue may be expressed and screened using standard antibody screening techniques in conjunction with antibodies raised against the normal endostatin gene product, as described, below. (For screening techniques, see, for example, Harlow and Lane, eds., 1988, "Antibodies: A Laboratory Manual", Cold Spring Harbor Press, Cold Spring Harbor.)

In cases where an endostatin mutation results in an expressed gene product with altered function (e.g., as a result of a missense or a frameshift mutation), a polyclonal set of anti-endostatin gene product antibodies are likely to cross-react with the mutant endostatin gene product. Library clones detected via their reaction with such labeled antibodies can be purified and subjected to sequence analysis according to methods well known to those of skill in the art.

Endostatin mutations or polymorphisms can further be detected using PCR amplification techniques. Primers can routinely be designed to amplify overlapping regions of the whole endostatin sequence including the promoter regulating region. In one embodiment, primers are designed to cover the exon-intron boundaries such that, coding regions can be scanned for mutations.

The invention also includes nucleic acid molecules, preferably DNA molecules, that are the complements of the nucleotide sequences of the preceding paragraphs.

In certain embodiments, the nucleic acid molecules of the invention are present as part of nucleic acid molecules comprising nucleic acid sequences that contain or encode heterologous (e.g., vector, expression vector, or fusion protein) sequences.

Endostatin gene products include those gene products encoded by nucleic acid molecules comprising the endostatin gene sequences described, above. In addition, endostatin gene products may include proteins that represent functionally equivalent gene products. Such an equivalent endostatin gene products may contain deletions, including internal deletions, additions, including additions yielding fusion proteins, or substitutions of amino acid residues within and/or adjacent to the amino acid sequence encoded by the endostatin gene sequences described, above, but that result in a "silent" change, in that the change produces a functionally equivalent endostatin gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Alternatively, where alteration of function is desired, deletion or non-conservative alterations can be engineered to produce altered endostatin gene products. Such alterations can, for example, alter one or more of the biological functions of the endostatin gene product. Further, such alterations can be selected so as to generate endostatin gene products that are better suited for expression, scale up, etc. in the host cells chosen. For example, cysteine residues can be deleted or substituted with another amino acid residue in order to eliminate disulfide bridges.

Peptides and/or proteins corresponding to one or more domains of an endostatin protein, as well as fusion proteins, in which an endostatin protein or a portion of an endostatin protein, such as a truncated endostatin protein, or peptide or an endostatin protein domain, is fused to an unrelated protein are also within the scope of this invention. Such proteins and peptides can be designed on the basis of the endostatin nucleotide sequence disclosed, above, and/or on the basis of the endostatin amino acid sequence disclosed herein. Fusion proteins include, but are not limited to, IgFc fusions which stabilize the endostatin protein or peptide and prolong half life in vivo; or fusions to any amino acid sequence that allows the fusion protein to be anchored to the cell membrane; or fusions of endostatin protein domains to an enzyme, fluorescent protein, luminescent protein, or a flag epitope protein or peptide which provides a marker function.

Endostatin proteins of the invention also include endostatin protein sequences wherein domains encoded by at least one exon of the cDNA sequence, or fragments thereof, have been deleted.

The endostatin protein sequences described above can include a domain which comprises a signal sequence that targets the endostatin gene product for secretion. As used herein, a signal sequence includes a peptide of at least about 15 or 20 amino acid residues in length which occurs at the N-terminus of secretory and membrane-bound proteins and which contains at least about 70% hydrophobic amino acid residues such as alanine, leucine, isoleucine, phenylalanine, proline, tyrosine, tryptophan, or valine. In a preferred embodiment, a signal sequence contains at least about 10 to 40 amino acid residues, preferably about 19–34 amino acid residues, and has at least about 60–80%, more preferably 65–75%, and more preferably at least about 70% hydrophobic residues. A signal sequence serves to direct a protein containing such a sequence to a lipid bilayer.

A signal sequence of a polypeptide of the invention can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described endostatin polypeptides having a signal sequence (that is, "immature" polypeptides), as well as to the endostatin signal sequences themselves and to the endostatin polypeptides in the absence of a signal sequence (i.e., the "mature" endostatin cleavage products). It is to be understood that endostatin polypeptides of the invention can further comprise polypeptides comprising any signal sequence having characteristics as described above and a mature endostatin polypeptide sequence.

The endostatin polypeptides of the invention can further comprise posttranslational modifications, including, but not limited to, glycosylations, acetylations, myristylations, and phosphorylations. If the native endostatin protein does not have recognition motifs that allow such modifications, it would be routine for one skilled in the art to introduce into an endostatin gene nucleotide sequences that encode motifs such as enzyme recognition signals so as to produce a modified endostatin gene product.

The endostatin gene products, peptide fragments thereof and fusion proteins thereof, may be produced by recombinant DNA technology using techniques well known in the art. Thus, methods for preparing the endostatin gene polypeptides, peptides, fusion peptide and fusion polypeptides of the invention by expressing nucleic acid containing endostatin gene sequences are described herein. Methods that are well known to those skilled in the art can be used to construct expression vectors containing endostatin gene product coding sequences and appropriate transcriptional and translational control signals. These methods include, for example, in vitro recombinant DNA techniques, synthetic techniques, and in vivo genetic recombination. See, e.g., the techniques described in Sambrook, et al., 1989, supra, and Ausubel, et al., 1989, supra. Alternatively, RNA capable of encoding endostatin gene product sequences may be chemically synthesized using, for example, synthesizers. See, e.g., the techniques described in "Oligonucleotide Synthesis", 1984, Gait, ed., IRL Press, Oxford.

A variety of host-expression vector systems may be utilized to express the endostatin gene coding sequences of the invention. Such host-expression systems represent vehicles by which the coding sequences of interest may be produced and subsequently purified, but also represent cells that may, when transformed or transfected with the appropriate nucleotide coding sequences, exhibit the endostatin gene product of the invention in situ. These include, but are not limited to, microorganisms such as bacteria (e.g., *E. coli, B. subtilis*) transformed with recombinant bacteriophage DNA, plasmid DNA or cosmid DNA expression vectors containing endostatin gene product coding sequences; yeast (e.g., Saccharomyces, Pichia) transformed with recombinant yeast expression vectors containing the endostatin gene product coding sequences; insect cell systems infected with recombinant virus expression vectors (e.g., baculovirus) containing the endostatin gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing endostatin gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the endostatin gene product being expressed. For example, when a large quantity of such a protein is to be produced, for the generation of pharmaceutical compositions of endostatin protein or for raising antibodies to endostatin protein, for example, vectors that direct the expression of high levels of fusion protein products that are readily purified may be desirable. Such vectors include, but are not limited, to the *E. coli* expression vector pUR278 (Ruther et al., 1983, EMBO J. 2, 1791), in which the endostatin gene product coding sequence may be ligated individually into the vector in frame with the lac Z coding region so that a fusion protein is produced; pIN vectors (Inouye and Inouye, 1985, Nucleic Acids Res. 13, 3101–3109; Van Heeke and Schuster, 1989, J. Biol. Chem. 264, 5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica, nuclear polyhedrosis virus (AcNPV) is used as a vector to express foreign genes. The virus grows in *Spodoptera frugiperda* cells. Endostatin gene coding sequences may be cloned individually into non-essential regions (for example the polyhedrin gene) of the virus and placed under control of an AcNPV promoter (for example the polyhedrin promoter). Successful insertion of endostatin gene coding sequences will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith, et al., 1983, J. Virol. 46, 584; Smith, U.S. Pat. No. 4,215,051).

In mammalian host cells, a number of viral-based expression systems may be utilized. In cases where an adenovirus is used as an expression vector, an endostatin gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing endostatin gene product in infected hosts. (e.g., See Logan and Shenk, 1984, Proc. Natl. Acad. Sci. USA 81, 3655–3659). Specific initiation signals may also be required for efficient translation of inserted endostatin gene product coding sequences. These signals include the ATG initiation codon and adjacent sequences. In cases where an entire endostatin gene, including an initiation codon and adjacent sequences, is inserted into the appropriate expression vector, no additional translational control signals may be needed. In cases where only a portion of the endostatin gene coding sequence is inserted, similar exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner, et al., 1987, Methods in Enzymol. 153, 516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, and WI38.

For long-term, high-yield production of recombinant proteins, stable expression is preferred. For example, cell lines that stably express the endostatin gene product may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the endostatin gene product. Such engineered cell lines may be particularly useful in screening and evaluation of compounds that affect the endogenous activity of the endostatin gene product.

A number of selection systems may be used, including, but not limited to, the herpes simplex virus thymidine kinase (Wigler, et al., 1977, Cell 11, 223), hypoxanthine-guanine phosphoribosyltransferase (Szybalska and Szybalski, 1962, Proc. Natl. Acad. Sci. USA 48, 2026), and adenine phosphoribosyltransferase (Lowy, et al., 1980, Cell 22, 817) genes can be employed in tk-, hgprt- or aprt-cells, respectively. Also, antimetabolite resistance can be used as the basis of selection for the following genes: dhfr, which confers resistance to methotrexate (Wigler, et al., 1980, Natl. Acad. Sci. USA 77, 3567; O'Hare, et al., 1981, Proc. Natl. Acad. Sci. USA 78, 1527); gpt, which confers resistance to mycophenolic acid (Mulligan and Berg, 1981, Proc. Natl. Acad. Sci. USA 78, 2072); neo, which confers resistance to the aminoglycoside G-418 (Colberre-Garapin, et al., 1981, J. Mol. Biol. 150, 1); and hygro, which confers resistance to hygromycin (Santerre, et al., 1984, Gene 30, 147).

Alternatively, any fusion protein may be readily purified by utilizing an antibody specific for the fusion protein being expressed. For example, a system described by Janknecht, et al. allows for the ready purification of non-denatured fusion proteins expressed in human cell lines (Janknecht, et al., 1991, Proc. Natl. Acad. Sci. USA 88, 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

Alternatively, the expression characteristics of an endogenous endostatin gene within a cell, cell line, or microorganism may be modified by inserting a heterologous DNA regulatory element into the genome of a stable cell line or cloned microorganism such that the inserted regulatory element is operatively linked with the endogenous endostatin gene. For example, an endogenous endostatin gene which is normally "transcriptionally silent", i.e., an endostatin gene which is normally not expressed, or is expressed only at very low levels in a cell, cell line, or microorganism, may be activated by inserting a regulatory element which is capable of promoting the expression of a normally expressed gene product in that cell, cell line, or microorganism. Alternatively, a transcriptionally silent, endogenous endostatin gene may be activated by insertion of a promiscuous regulatory element that works across cell types.

A heterologous regulatory element may be inserted into a stable cell line or cloned microorganism, such that it is operatively linked with an endogenous endostatin gene, using techniques, such as targeted homologous recombination, which are well known to those of skill in the art, and described e.g., in Chappel, U.S. Pat. No. 5,272,071; PCT publication No. WO 91/06667, published May 16, 1991.

Endostatin gene products also can be expressed in transgenic animals. Animals of any species, including, but not limited to, mice, rats, rabbits, guinea pigs, pigs, micro-pigs, goats, sheep, and non-human primates, e.g., baboons, monkeys, and chimpanzees may be used to generate endostatin transgenic animals. The term "transgenic," as used herein, refers to animals expressing endostatin gene sequences from a different species (e.g., mice expressing human or canine endostatin sequences), as well as animals that have been genetically engineered to overexpress endogenous (i.e., same species) endostatin sequences or animals that have been genetically engineered to no longer express endogenous endostatin gene sequences (i.e., "knock-out" animals), and their progeny.

Any technique known in the art may be used to introduce an endostatin gene transgene into animals to produce the founder lines of transgenic animals. Such techniques include, but are not limited to, pronuclear microinjection (Hoppe and Wagner, 1989, U.S. Pat. No. 4,873,191); retrovirus mediated gene transfer into germ lines (van der Putten, et al., 1985, Proc. Natl. Acad. Sci., USA 82, 6148–6152); gene targeting in embryonic stem cells (Thompson, et al., 1989, Cell 56, 313–321); electroporation of embryos (Lo, 1983, Mol. Cell. Biol. 3, 1803–1814); and sperm-mediated gene transfer (Lavitrano et al., 1989, Cell 57, 717–723). (For a review of such techniques, see Gordon, 1989, Transgenic Animals, Intl. Rev. Cytol. 115, 171–229.)

Any technique known in the art may be used to produce transgenic animal clones containing an endostatin transgene, for example, nuclear transfer into enucleated oocytes of nuclei from cultured embryonic, fetal or adult cells induced to quiescence (Campbell, et al., 1996, Nature 380, 64–66; Wilmut, et al., Nature 385, 810–813).

The present invention provides for transgenic animals that carry an endostatin transgene in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, et al., 1992, Proc. Natl. Acad. Sci. USA 89, 6232–6236). The regulatory sequences required for such a cell-type specific activation will depend upon the particular cell type of interest, and will be apparent to those of skill in the art. When it is desired that the endostatin gene transgene be integrated into the chromosomal site of the endogenous endostatin gene, gene targeting is preferred. Briefly, when such a technique is to be utilized, vectors containing some nucleotide sequences homologous to the endogenous endostatin gene are designed for the purpose of integrating, via homologous recombination with chromosomal sequences, into and disrupting the function of the nucleotide sequence of the endogenous endostatin gene. The transgene may also be selectively introduced into a particular cell type, thus inactivating the endogenous endostatin gene in only that cell type, by following, for example, the teaching of Gu, et al. (Gu, et al., 1994, Science 265, 103–106). The regulatory sequences required for such a cell-type specific inactivation will depend upon the particular cell type of interest, and will be apparent to those of skill in the art.

Once transgenic animals have been generated, the phenotypic expression of the recombinant endostatin gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include, but are not limited to, Northern blot analysis of tissue samples obtained from the animal, in situ hybridization analysis, and RT-PCR (reverse transcriptase PCR). Samples of endostatin gene-expressing tissue, may also be evaluated immunocytochemically using antibodies specific for the endostatin transgene product.

Endostatin gene products, or peptide fragments thereof, can be prepared for a variety of uses. For example, such gene products, or peptide fragments thereof, can be used for the generation of antibodies, in diagnostic assays, or for mapping and the identification of other cellular or extracellular gene products involved in the regulation of an angiogenesis-related disorder, such as cancer. Such endostatin gene products include, but are not limited to, soluble derivatives such as peptides or polypeptides corresponding to one or more domains of the endostatin gene product, particularly endostatin gene products that are modified such that they are deleted for one or more hydrophobic domains. Alternatively, antibodies to the endostatin protein or anti-idiotypic antibodies that mimic the endostatin gene product (including Fab fragments), antagonists or agonists can be used to treat angiogenesis-related disorders, such as cancer. In yet another approach, nucleotide constructs encoding such endostatin gene products can be used to genetically engineer host cells to express such endostatin gene products in vivo; these genetically engineered cells can function as "bioreactors" in the body delivering a continuous supply of endostatin gene product, endostatin peptides or soluble endostatin polypeptides.

Described herein are methods for the production of antibodies capable of specifically recognizing one or more endostatin gene product epitopes or epitopes of conserved variants or peptide fragments of the gene products.

Such antibodies may include, but are not limited to, polyclonal antibodies, monoclonal antibodies (mAbs), canine, human, humanized or chimeric antibodies, single chain antibodies, Fab fragments, F(ab')2 fragments, fragments produced by a Fab expression library, anti-idiotypic (anti-id) antibodies, and epitope-binding fragments of any of the above. Such antibodies may be used, for example, in the detection of an endostatin gene product in an biological sample and may, therefore, be utilized as part of a diagnostic or prognostic technique whereby subjects may be tested for abnormal levels of endostatin gene products, and/or for the presence of abnormal forms of such gene products. Such antibodies may also be utilized in conjunction with, for example, compound screening schemes, as described below, for the evaluation of the effect of test compounds on endostatin gene product levels and/or activity. Additionally, such antibodies can be used in conjunction with the gene therapy techniques described below, for example, to evaluate the normal and/or engineered endostatin-expressing cells prior to their introduction into the subject.

Anti-endostatin gene product antibodies may additionally be used as a method for the inhibition of abnormal endostatin gene product activity. Thus, such antibodies may, be utilized as part of treatment methods for an angiogenesis-related disorder, e.g., cancer.

For the production of antibodies against an endostatin gene product, various host animals may be immunized by injection with an endostatin gene product, or a portion thereof. Such host animals may include, but are not limited to, rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as an endostatin gene product, or an antigenic functional derivative thereof. For the production of polyclonal antibodies, host animals such as those described above, may be immunized by injection with endostatin gene product supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, Nature 256, 495–497; and U.S. Pat. No. 4,376,110), the human B-cell hybridoma technique (Kosbor et al., 1983, Immunology Today 4, 72; Cole et al., 1983, Proc. Natl. Acad. Sci. USA 80, 2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison (1985) *Science* 229:1202–1207; Oi et al. (1986) *Bio/Techniques* 4:214; U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immunol.* 13:65–93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. In addition, companies such as Abgenix, Inc. (Fremont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) *Bio/technology* 12:899–903).

Alternatively, techniques described for the production of single chain antibodies (U.S. Pat. No. 4,946,778; Bird, 1988, Science 242, 423–426; Huston, et al., 1988, Proc. Natl. Acad. Sci. USA 85, 5879–5883; and Ward, et al., 1989, Nature 334, 544–546) can be adapted to produce single chain antibodies against endostatin gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to, the F(ab+)2 fragments, which can be produced by pepsin digestion of the antibody molecule and the Fab fragments, which can be generated by reducing the disulfide bridges of the F(ab')2 fragments. Alternatively, Fab expression libraries may be constructed (Huse, et al., 1989, Science, 246, 1275–1281) to allow rapid and easy identification of monoclonal Fab fragments with the desired specificity.

Described herein are various applications of endostatin gene sequences, endostatin gene products, including peptide fragments and fusion proteins thereof, and of antibodies directed against endostatin gene products and peptide fragments thereof. Such applications include, for example, prognostic and diagnostic evaluation of an angiogenesis-related disorder, e.g., cancer, and the identification of subjects with a predisposition to such disorders, as described, below, in Section. Additionally, such applications include methods for the identification of compounds that modulate the expression of an endostatin gene and/or the synthesis or activity of an endostatin gene product, as described below, and for the treatment of an angiogenesis-related disorder, e.g. cancer, as described, below.

In addition, endostatin gene sequences and gene products, including peptide fragments and fusion proteins thereof, and antibodies directed against endostatin gene products and peptide fragments thereof, have applications for purposes independent of the role endostatin may have in angiogenesis-related disorders and processes. For example, endostatin gene products, including peptide fragments, as well as endostatin-specific antibodies, can be used for construction of fusion proteins to facilitate recovery, detection, or localization of another protein of interest. In addition, endostatin genes and gene products can be used for genetic mapping, i.e., refining the genetic map. For example, antibodies specific to endostatin can be used as probes to detect expression of human endostatin in somatic cell hybrids containing human chromosomes, or portions of human chromosomes. Such endostatin-specific antibodies can be used to identify cells that contain the endostatin chromosomal region. This method can be used, for example, to localize a gene or trait of interest to this region of the chromosome.

Endostatin gene sequences and gene products can be used for mapping and refining a chromosomal map. The endostatin sequence can be used to develop new genetic markers to further refine chromosomal intervals that are associated with various angiogensis-related disorders, including, but not limited to, cancer. As will be apparent to the skilled artisan, nucleic acid sequences within a genetic interval associated with a disease can be scanned for new markers, such as microsatellites. Microsatellites, also known as simple-sequence repeats (SSRs), are hypervariable tandem-sequence repeats consisting of di-, tri-, or tetranucleotide repeats of 1–5 nucleotides. Such microsatellites make excellent genetic markers for linkage studies since they are distributed ubiquitously throughout the human genome, are highly variable in repeat length, and tend to be highly polymorphic. Relatively common microsatellites (e.g., (CA)n dinucleotide repeats) occur approximately every 300–500 kb. In addition to microsatellite repeats, the region can be scanned for other types of polymorphic sites useful for fine mapping, such as minisatellites (9–64 nucleotide repeats), restriction fragment length polymorphisms (RFLPs), and single nucleotide polymorphisms, which occur much less frequently. Once a polymorphic site is identified in a new sequence, PCR primers that flank the polymorphic site can be synthesized and used to amplify the microsatellite or other polymorphic site. The length of the repeat can then determined by resolving the PCR product on a polyacrylamide sequencing gel. Genomic DNA from human populations can then be analyzed for the simple-sequence length polymorphisms (SSLPs) to determine the frequency and variability of the repeat. Once a high quality SSLP is found, linkage analysis can be performed on an affected population to determine whether an angiogenesis-related disorder, such as cancer, is linked to the new marker. Other techniques, such as Southern blot hybridization and ligase-chain reaction (LCR), can be used in addition to, or in conjunction with, PCR-based methods to analyze polymorphisms in genomic populations (see, Current Protocols in Human Genetics, Dracopoli et al. (eds.) John Wiley & Sons, 1998).

In another embodiment, an endostatin gene, protein or a fragment or domain thereof, can be used for construction of fusion proteins. Finally, endostatin nucleic acids and gene products have generic uses, such as supplemental sources of nucleic acids, proteins and amino acids for food additives or cosmetic products.

Portions or fragments of the cDNA sequences identified herein (and the corresponding complete gene sequences) can be used in numerous ways as polynucleotide reagents. For example, these sequences can be used to: (i) screen for endostatin gene-specific mutations or polymorphisms, (ii) map their respective genes on a chromosome and, thus, locate gene regions associated with genetic disease; (iii) identify an individual organism from a minute biological sample (tissue typing); and (iv) aid in forensic identification of a biological sample. These applications are described in the subsections below.

A variety of methods can be employed to screen for the presence of endostatin gene-specific mutations or polymorphisms (including polymorphisms flanking an endostatin gene, e.g., ones that cosegregate with a particular endostatin allele) and to detect and/or assay levels of endostatin nucleic acid sequences.

Mutations or polymorphisms within or flanking the endostatin gene can be detected by utilizing a number of techniques. Nucleic acid from any nucleated cell, or any cell that expresses the endostatin gene of interest, can be used as the starting point for such assay techniques, and may be isolated according to standard nucleic acid preparation procedures that are well known to those of skill in the art.

Endostatin nucleic acid sequences may be used in hybridization or amplification assays of biological samples to detect abnormalities involving endostatin gene structure, including point mutations, insertions, deletions, inversions, translocations and chromosomal rearrangements. Such assays may include, but are not limited to, Southern analyses, single-stranded conformational polymorphism analyses (SSCP), and PCR analyses.

Diagnostic methods for the detection of endostatin gene-specific mutations or polymorphisms can involve, for example, contacting and incubating nucleic acids obtained from a sample, e.g., derived from a patient sample or other appropriate cellular source with one or more labeled nucleic acid reagents including recombinant DNA molecules, cloned genes or degenerate variants thereof, such as described, above, under conditions favorable for the specific annealing of these reagents to their complementary sequences within or flanking the endostatin gene. The diagnostic methods of the present invention further encompass contacting and incubating nucleic acids for the detection of single nucleotide mutations or polymorphisms of the endostatin gene. Preferably, these nucleic acid reagent sequences within the endostatin gene, or chromosome nucleotide sequences flanking the endostatin gene are 15 to 30 nucleotides in length.

After incubation, all non-annealed nucleic acids are removed from the nucleic acid:endostatin molecule hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described above, are easily removed. Detection of the remaining, annealed, labeled endostatin nucleic acid reagents is accomplished using standard techniques well-known to those in the art. The endostatin gene sequences to which the nucleic acid reagents have annealed can be compared to the annealing pattern expected from a normal endostatin gene sequence in order to determine whether an endostatin gene mutation is present.

In a preferred embodiment, endostatin mutations or polymorphisms can be detected by using a microassay of endostatin nucleic acid sequences immobilized to a substrate or "gene chip" (see, e.g. Cronin et al., 1996, Human Mutation 7:244–255).

Alternative diagnostic methods for the detection of endostatin gene-specific nucleic acid molecules (or endostatin flanking sequences), in patient samples or other appropriate cell sources, may involve their amplification, e.g., by PCR (the experimental embodiment set forth in Mullis, 1987, U.S. Pat. No. 4,683,202), followed by the analysis of the amplified molecules using techniques well known to those of skill in the art, such as, for example, those listed above. The resulting amplified sequences can be compared to those that would be expected if the nucleic acid being amplified contained only normal copies of the endostatin gene in order to determine whether an endostatin gene mutation or polymorphism in linkage disequilibrium with a disease-causing endostatin allele exists.

Additionally, well-known genotyping techniques can be performed to identify individual organisms carrying endostatin gene mutations. Such techniques include, for example, the use of restriction fragment length polymorphisms (RFLPs), which involve sequence variations in one of the recognition sites for the specific restriction enzyme used.

Further, improved methods for analyzing DNA polymorphisms, which can be utilized for the identification of endostatin gene-specific mutations, have been described that capitalize on the presence of variable numbers of short, tandemly repeated DNA sequences between the restriction enzyme sites. For example, Weber (U.S. Pat. No. 5,075,217) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers that are so closely spaced exhibit a high frequency co-inheritance, and are extremely useful in the identification of genetic mutations, such as, for example, mutations within the endostatin gene, and the diagnosis of diseases and disorders related to endostatin mutations.

Also, Caskey et al. (U.S. Pat. No. 5,364,759) describe a DNA profiling assay for detecting short tri and tetra nucleotide repeat sequences. The process includes extracting the DNA of interest, such as the endostatin gene, amplifying the extracted DNA, and labeling the repeat sequences to form a genotypic map of the individual organism's DNA.

Other methods well known in the art may be used to identify single nucleotide polymorphisms (SNPs), including biallelic SNPs or biallelic markers which have two alleles, both of which are present at a fairly high frequency in a population. Conventional techniques for detecting SNPs include, e.g., conventional dot blot analysis, SSCP analysis (see, e.g., Orita et al., 1989, *Proc. Natl. Acad. Sci. USA* 86:2766–2770), denaturing gradient gel electrophoresis (DGGE), heteroduplex analysis, mismatch cleavage detection, and other routine techniques well known in the art (see, e.g., Sheffield et al., 1989, *Proc. Natl. Acad. Sci.* 86:5855–5892; Grompe, 1993, *Nature Genetics* 5:111–117). Alternative, preferred methods of detecting and mapping SNPs involve microsequencing techniques wherein an SNP site in a target DNA is detecting by a single nucleotide primer extension reaction (see, e.g., Goelet et al., PCT Publication No. WO92/15712; Mundy, U.S. Pat. No. 4,656,127; Vary and Diamond, U.S. Pat. No. 4,851,331; Cohen et al., PCT Publication No. WO91/02087; Chee et al., PCT Publication No. WO95/11995; Landegren et al., 1988, Science 241:1077–1080; Nicerson et al., 1990, Proc. Natl. Acad. Sci. U.S.A. 87:8923–8927; Pastinen et al., 1997, Genome Res. 7:606–614; Pastinen et al., 1996, Clin. Chem. 42:1391–1397; Jalanko et al., 1992, Clin. Chem. 38:39–43; Shumaker et al., 1996, Hum. Mutation 7:346–354; Caskey et al., PCT Publication No. WO 95/00669).

The level of endostatin expression also can be determined by first assaying for the level of gene expression. For example, RNA from a cell type or tissue known, or suspected, to express the endostatin gene, such as liver, may be isolated and tested utilizing hybridization or PCR techniques such as are described, above. The isolated cells can be derived from cell culture or from a subject. The analysis of cells taken from culture may be a necessary step in the assessment of cells to be used as part of a cell-based gene therapy technique or, alternatively, to test the effect of compounds on the expression of the endostatin gene.

In one embodiment of such a detection scheme, a cDNA molecule is synthesized from an RNA molecule of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the endostatin gene nucleic acid reagents described above. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such endostatin gene expression assays in situ, i.e., directly upon tissue sections (fixed and/or frozen) of subject tissue obtained from biopsies or resections, such that no nucleic acid purification is necessary. Nucleic acid reagents such as those described above, may be used as probes and/or primers for such in situ procedures (see, for example, Nuovo, G. J., 1992, "PCR In Situ Hybridization: Protocols And Applications", Raven Press, New York).

Alternatively, if a sufficient quantity of the appropriate cells can be obtained, standard Northern analysis can be performed to determine the level of mRNA expression of the endostatin gene.

Once the sequence (or a portion of the sequence) of a gene has been isolated, this sequence can be used to map the location of the gene on a chromosome. Accordingly, nucleic acid molecules described herein, or fragments thereof, can be used to map the location of the corresponding genes on a chromosome. The mapping of the sequences to chromosomes is an important first step in correlating these sequences with genes associated with disease.

Briefly, genes can be mapped to chromosomes by preparing PCR primers (preferably 15–25 bp in length) from the sequence of a gene of the invention. Computer analysis of the sequence of a gene of the invention can be used to rapidly select primers that do not span more than one exon in the genomic DNA, thus simplifying the amplification process. These primers can then be used for PCR screening of somatic cell hybrids containing individual human chromosomes. Only those hybrids containing the human gene corresponding to the gene sequences will yield an amplified fragment. For a review of this technique, see D'Eustachio et al., 1983, *Science,* 220:919–924.

PCR mapping of somatic cell hybrids is a rapid procedure for assigning a particular sequence to a particular chromosome. Three or more sequences can be assigned per day using a single thermal cycler. Using the nucleic acid sequences of the invention to design oligonucleotide primers, sublocalization can be achieved with panels of fragments from specific chromosomes. Other mapping strategies which can similarly be used to map a gene to its chromosome include in situ hybridization (described in Fan et al., 1990, Proc. Natl. Acad. Sci. USA 87:6223–27), pre-screening with labeled flow-sorted chromosomes (Popp S, et al., 1993, Hum Genet., 92(6):527–32) and pre-selection by hybridization to chromosome specific cDNA libraries. Fluorescence in situ hybridization (FISH) of a DNA sequence to a metaphase chromosomal spread can further be used to provide a precise chromosomal location in one step. (For a review of this technique, see Verma et al., Human Chromosomes: A Manual of Basic Techniques, Pergamon Press, New York, 1988.)

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al.,1987, Nature 325:783–787.

Moreover, differences in the DNA sequences between individual organisms affected and unaffected with a disease associated with a gene of the invention can be determined. If a mutation is observed in some or all of the affected individual organisms but not in any unaffected individual organisms, then the mutation is likely to be the causative agent of the particular disease. Comparison of affected and unaffected individual organisms generally involves first looking for structural alterations in the chromosomes such as deletions or translocations that are visible from chromosome spreads or detectable using PCR based on that DNA sequence. Ultimately, complete sequencing of genes from several individual organisms can be performed to confirm the presence of a mutation and to distinguish mutations from polymorphisms.

The nucleic acid sequences of the present invention also can be used to identify individual organisms from minute biological samples. The United States military, for example, is considering the use of restriction fragment length polymorphism (RFLP) for identification of its personnel. In this technique, an individual organism's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual organism's genome. Thus, the nucleic acid sequences described herein can be used to prepare two PCR primers from the 5' and 3' ends of the sequences. These primers can then be used to amplify an individual organism's DNA and subsequently sequence it.

Panels of corresponding DNA sequences from individual organisms, prepared in this manner, can provide unique individual identifications, as each individual organism will have a unique set of such DNA sequences due to allelic differences. The sequences of the present invention can be used to obtain such identification sequences from individual organisms and from tissue. The nucleic acid sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual organism can be compared for identification purposes. Because greater numbers of polymorphisms occur in the noncoding regions, fewer sequences are necessary to differentiate individuals.

If a panel of reagents from the nucleic acid sequences described herein is used to generate a unique identification database for an individual, those same reagents can later be used to identify tissue from that individual. Using the unique identification database, positive identification of the individual organism, living or dead, can be made from extremely small tissue samples.

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual organism). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individual organisms using this technique. Examples of polynucleotide reagents include the nucleic acid sequences of the invention or portions thereof, e.g., fragments derived from noncoding regions having a length of at least 20 or 30 bases.

The nucleic acid sequences described herein can further be used to provide polynucleotide reagents, e.g., labeled or labelable probes which can be used in, for example, an in situ hybridization technique, to identify a specific tissue, e.g., liver tissue. This can be very useful in cases where a forensic pathologist is presented with a tissue of unknown origin. Panels of such probes can be used to identify tissue by species and/or by organ type.

Antibodies directed against unimpaired or mutant endostatin gene products or conserved variants or peptide fragments thereof, which are discussed, above, may also be used as diagnostics and prognostics for an angiogenesis-related disorder, e.g., cancer, as described herein. Such methods may be used to detect abnormalities in the level of endostatin gene product synthesis or expression, or abnormalities in the structure, temporal expression, and/or physical location of endostatin gene product. The antibodies and immunoassay methods described below have, for example, important in vitro applications in purifying endostatin gene products and in assessing the efficacy of treatments for angiogenesis-related disorders, e.g., cancer. Antibodies, or fragments of antibodies, such as those described below, may be used to screen potentially therapeutic compounds in vitro to determine their effects on endostatin gene expression and endostatin peptide production. The compounds that have beneficial effects on an angiogenesis-related disorder, e.g., cancer, can be identified, and a therapeutically effective dose determined.

In vitro immunoassays may also be used, for example, to assess the efficacy of cell-based gene therapy for an angiogenesis-related disorder, e.g., cancer. Antibodies directed against endostatin peptides may be used in vitro to determine, for example, the level of endostatin gene expression achieved in cells genetically engineered to produce endostatin peptides. In the case of intracellular endostatin gene products, such an assessment is done, preferably, using cell lysates or extracts. Such analysis allows for a determination of the number of transformed cells necessary to achieve therapeutic efficacy in vivo, as well as optimization of the gene replacement protocol.

The tissue or cell type to be analyzed will generally include those that are known, or suspected, to express the endostatin gene. The protein isolation methods employed herein may, for example, be such as those described in Harlow and Lane (1988, "Antibodies: A Laboratory Manual", Cold Spring Harbor Laboratory Press, Cold Spring Harbor, N.Y.). The isolated cells can be derived from cell culture or from a subject. The analysis of cells taken from culture may be a necessary step in the assessment of cells to be used as part of a cell-based gene therapy technique or, alternatively, to test the effect of compounds on the expression of the endostatin gene.

Preferred diagnostic methods for the detection of endostatin gene products or conserved variants or peptide fragments thereof, may involve, for example, immunoassays wherein the endostatin gene products or conserved variants or peptide fragments are detected by their interaction with an anti-endostatin gene product-specific antibody.

For example, antibodies, or fragments of antibodies, such as those described, above, useful in the present invention may be used to quantitatively or qualitatively detect the presence of endostatin gene products or conserved variants or peptide fragments thereof. This can be accomplished, for example, by immunofluorescence techniques employing a fluorescently labeled antibody (see below, this section) coupled with light microscopic, flow cytometric, or fluorimetric detection. Such techniques are especially preferred for endostatin gene products that are expressed on the cell surface.

The antibodies (or fragments thereof) useful in the present invention may, additionally, be employed histologically, as in immunofluorescence or immunoelectron microscopy, for in situ detection of endostatin gene products or conserved variants or peptide fragments thereof. In situ detection may be accomplished by removing a histological specimen from a subject, and applying thereto a labeled antibody of the present invention. The antibody (or fragment) is preferably applied by overlaying the labeled antibody (or fragment) onto a biological sample. Through the use of such a procedure, it is possible to determine not only the presence of the endostatin gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays for endostatin gene products or conserved variants or peptide fragments thereof will typically comprise incubating a sample, such as a biological fluid, a tissue extract, freshly harvested cells, or lysates of cells, that have been incubated in cell culture, in the presence of a detectably labeled antibody capable of identifying endostatin gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled endostatin gene specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-endostatin gene product antibody may be determined according to well known methods. Those skilled in the art will be able to determine operative and optimal assay conditions for each determination by employing routine experimentation.

One of the ways in which the endostatin gene peptide-specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2, 1–7, Microbiological Associates Quarterly Publication, Walkersville, Md.); Voller, A. et al., 1978, J. Clin. Pathol. 31, 507–520; Butler, J. E., 1981, Meth. Enzymol. 73, 482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, β-glycerophosphate, dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase. The detection can be accomplished by calorimetric methods that employ a chromogenic substrate for the enzyme. Detection may also be accomplished by visual comparison of the extent of enzymatic reaction of a substrate in comparison with similarly prepared standards.

Detection also may be accomplished using any of a variety of other immunoassays. For example, by radioactively labeling the antibodies or antibody fragments, it is possible to detect endostatin gene peptides through the use of a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The following assays are designed to identify compounds that bind to an endostatin gene product, proteins, e.g., intracellular proteins or portions of proteins that interact with an endostatin gene product, compounds that interfere with the interaction of an endostatin gene product with intracellular proteins and compounds that modulate the activity of an endostatin gene (i.e., modulate the level of endostatin gene expression and/or modulate the level of endostatin gene product activity). Assays may additionally be utilized that identify compounds that bind to endostatin gene regulatory sequences (e.g., promoter sequences; see e.g., Platt, 1994, J. Biol. Chem. 269, 28558–28562), and that may modulate the level of endostatin gene expression. Compounds may include, but are not limited to, small organic molecules, such as ones that are able to cross the blood-brain barrier, gain entry into an appropriate cell and affect expression of the endostatin gene or some other gene involved in an endostatin regulatory pathway, or intracellular proteins.

Methods for the identification of such intracellular proteins are described, below. Such intracellular proteins may be involved in the control and/or regulation of mood. Further, among these compounds are compounds that affect the level of endostatin gene expression and/or endostatin gene product activity and that can be used in the therapeutic treatment of endostatin disorders, e.g., cancer, as described, below.

Compounds may include, but are not limited to, peptides such as, for example, soluble peptides, including, but not limited to, Ig-tailed fusion peptides, and members of random peptide libraries; (see, e.g., Lam, et al., 1991, Nature 354, 82–84; Houghten, et al., 1991, Nature 354, 84–86), and combinatorial chemistry-derived molecular library made of D- and/or L-configuration amino acids, phosphopeptides (including, but not limited to members of random or partially degenerate, directed phosphopeptide libraries; see, e.g., Songyang, et al., 1993, Cell 72, 767–778), antibodies (including, but not limited to, polyclonal, monoclonal, human, humanized, anti-idiotypic, chimeric or single chain antibodies, and FAb, F(ab□)2 and FAb expression library fragments, and epitope-binding fragments thereof), and small organic or inorganic molecules.

Such compounds may also comprise compounds, in particular drugs or members of classes or families of drugs, known to ameliorate or exacerbate the symptoms of an angiogenesis-related disorder. Such compounds include, but are not limited to, angiogenesis inhibitors: metalloproteinase inhibitors, FGF and VEGF receptor inhibitors, COX-2 inhibitors, INF, IL-12, Taxol, vinblastine, thalidomide etc. Preferably such compounds are utilized in a manner (e.g., different dosage, mode of administration, and/or co-administration with one or more additional compounds) that differs from the manner in which such compounds have been administered previously.

Compounds identified via assays such as those described herein may be useful, for example, in elaborating the biological function of the endostatin gene product, and for ameliorating angiogenesis-related disorders, e.g., cancer. For example, compounds identified via such techniques can provide lead compounds to be tested for an ability to modulate an endostatin-mediated process and/or to ameliorate symptoms of a angiogenesis-related disorder. Assays for testing the effectiveness of compounds, identified by, for example, techniques such as those described above, are discussed, below.

In vitro systems may be designed to identify compounds that bind endostatin gene products of the invention, such as, for example, endostatin polypeptides. Compounds identified may be useful, for example, in modulating the activity of unimpaired and/or mutant endostatin gene products, may be useful in elucidating the biological function of the endostatin gene product, may be utilized in screens for identifying compounds that disrupt normal endostatin gene product interactions, or may in themselves disrupt such interactions, and can provide lead compounds to be further tested for an ability to modulate an endostatin-mediated process and/or to ameliorate symptoms of an angiogenesis-related disorder.

The principle of the assays used to identify compounds that bind to endostatin gene products involves preparing a reaction mixture of the endostatin gene product and the test compound under conditions and for a time sufficient to allow the two components to interact and bind, thus forming a complex that can be removed and/or detected in the reaction mixture. These assays can be conducted in a variety of ways. For example, one method to conduct such an assay would involve anchoring an endostatin gene product or the test substance onto a solid phase and detecting endostatin gene product/test compound complexes anchored on the solid phase at the end of the reaction. In one embodiment of such a method, the endostatin gene product may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for endostatin gene product or the test compound to anchor any complexes formed in solution, and a labeled antibody specific for the other component of the possible complex to detect anchored complexes.

Any method suitable for detecting protein—protein interactions may be employed for identifying endostatin protein—protein interactions.

Among the traditional methods that may be employed are co-immunoprecipitation, cross-linking and co-purification through gradients or chromatographic columns. Utilizing procedures such as these allows for the identification of proteins, including intracellular proteins, that interact with endostatin gene products. Once isolated, such a protein can be identified and can be used in conjunction with standard techniques, to identify proteins it interacts with. For example, at least a portion of the amino acid sequence of a protein that interacts with the endostatin gene product can be ascertained using techniques well known to those of skill in the art, such as via the Edman degradation technique (see, e.g., Creighton, 1983, "Proteins: Structures and Molecular Principles," W. H. Freeman & Co., New York, pp.34–49). The amino acid sequence obtained may be used as a guide for the generation of oligonucleotide mixtures that can be used to screen for gene sequences encoding such proteins. Screening made be accomplished, for example, by standard hybridization or PCR techniques. Techniques for the generation of oligonucleotide mixtures and the screening are well-known. (See, e.g., Ausubel, supra, and 1990, "PCR Protocols: A Guide to Methods and Applications," Innis, et al., eds. Academic Press, Inc., New York).

Additionally, methods may be employed that result in the simultaneous identification of genes that encode a protein which interacts with an endostatin protein. These methods include, for example, probing expression libraries with labeled endostatin protein, using endostatin protein in a manner similar to the well known technique of antibody probing of gt11 libraries.

One method that detects protein interactions in vivo, the two-hybrid system, is described in detail for illustration only and not by way of limitation. One version of this system has been described (Chien, et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to the endostatin gene product and the other consists of the transcription activator protein's activation domain fused to an unknown protein that is encoded by a cDNA that has been recombined into this plasmid as part of a cDNA library. The DNA-binding domain fusion plasmid and the cDNA library are transformed into a strain of the yeast Saccharomyces cerevisiae that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, endostatin gene products may be used as the bait gene product. Total genomic or cDNA sequences are fused to the DNA encoding an activation domain. This library and a plasmid encoding a hybrid of a bait endostatin gene product fused to the DNA-binding domain are co-transformed into a yeast reporter strain, and the resulting transformants are screened for those that express the reporter gene. For example, and not by way of limitation, a bait endostatin gene sequence, such as the open reading frame of the endostatin gene, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with the bait endostatin gene product can be made using methods routinely practiced in the art. According to the particular system described herein, for example, the cDNA fragments can be inserted into a vector such that they are translationally fused to the transcriptional activation domain of GAL4. This library can be co-transformed along with the bait endostatin gene-GAL4 fusion plasmid into a yeast strain that contains a lacZ gene driven by a promoter that contains GAL4 activation sequence. A cDNA encoded protein, fused to GAL4 transcriptional activation domain, that interacts with bait endostatin gene product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait endostatin gene-interacting protein using techniques routinely practiced in the art.

Endostatin gene products of the invention may, in vivo, interact with one or more macromolecules, including cellular or extracellular macromolecules, such as proteins. Such macromolecules may include, but are not limited to, other proteins, such as cellular receptors, or nucleic acid molecules and those proteins identified via methods such as those described, above. For example, the endostatin gene product may interact with a receptor as a peptide hormone or neuropeptide. For purposes of this discussion, the macromolecules are referred to herein as "binding partners". Compounds that disrupt endostatin binding in this way may be useful in regulating the activity of the endostatin gene product, especially mutant endostatin gene products. For example, such compounds may interfere with the interaction of the endostatin gene product, with its receptor. Such compounds may include, but are not limited to, molecules such as peptides, and the like, as described, for example, above, which would be capable of gaining access to an endostatin gene product.

The basic principle of the assay systems used to identify compounds that interfere with the interaction between the endostatin gene product and its binding partner or partners involves preparing a reaction mixture containing the endostatin gene product, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the endostatin gene product and its binding partner. Control reaction mixtures are incubated without the test compound or with a placebo. The formation of any complexes between the endostatin gene protein and the binding partner is then detected. The formation of a complex in the control reaction, but not in the reaction mixture containing the test compound, indicates that the compound interferes with the interaction of the endostatin gene protein and the interactive binding partner. Additionally, complex formation within reaction mixtures containing the test compound and normal endostatin gene protein may also be compared to complex formation within reaction mixtures containing the test compound and a mutant endostatin gene protein. This comparison may be important in those cases wherein it is desirable to identify compounds that disrupt interactions of mutant but not normal endostatin gene proteins.

The assay for compounds that interfere with the interaction of the endostatin gene products and binding partners can be conducted in a heterogeneous or homogeneous format. Heterogeneous assays involve anchoring either the endostatin gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the endostatin gene products and the binding partners, e.g., by competition, can be identified by conducting the reaction in the presence of the test substance; i.e., by adding the test substance to the reaction mixture prior to or simultaneously with the endostatin gene protein and interactive intracellular binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the endostatin gene product or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the endostatin gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. In this approach, a preformed complex of the endostatin gene protein and the interactive binding partner is prepared in which either the endostatin gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt a endostatin gene protein/binding partner interaction can be identified.

In a particular embodiment, the endostatin gene product can be prepared for immobilization using recombinant DNA techniques described above. For example, the endostatin coding region can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art and described above. This antibody can be labeled with the radioactive isotope 1251, for example, by methods routinely practiced in the art. In a heterogeneous assay, e.g., the GST-endostatin fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the endostatin gene protein and the interactive binding partner can be detected by measuring the amount of radioactivity that remains associated with the glutathione-agarose beads. A successful inhibition of the interaction by the test compound will result in a decrease in measured radioactivity.

Alternatively, the GST-endostatin gene fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the endostatin gene product/binding partner interaction can be detected by adding the labeled antibody and measuring the radioactivity associated with the beads.

In another embodiment of the invention, these same techniques can be employed using peptide fragments that correspond to the binding domains of the endostatin protein and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this section, above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the segments can be engineered to express peptide fragments of the protein, which can then be tested for binding activity and purified or synthesized.

For example, and not by way of limitation, an endostatin gene product can be anchored to a solid material as described, above, in this section by making a GST-endostatin fusion protein and allowing it to bind to glutathione agarose beads. The interactive binding partner obtained can be labeled with a radioactive isotope, such as 35S, and cleaved with a proteolytic enzyme such as trypsin. Cleavage products can then be added to the anchored GST-endostatin fusion protein and allowed to bind. After washing away unbound peptides, labeled bound material, representing the binding partner binding domain, can be eluted, purified, and analyzed for amino acid sequence by well-known methods. Peptides so identified can be produced synthetically or fused to appropriate facilitative proteins using recombinant DNA technology.

Compounds including, but not limited to, binding compounds identified via assay techniques such as those described, above, can be tested for the ability to ameliorate symptoms of an angiogenesis-related disorder, e.g., angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; wound granulation; corornary collaterals; cerebral collaterals; arteriovenous malformations; ischemic limb angiogenesis; diabetic neovascularization; macular degeneration; fractures; vasculogenesis; hematopoiesis; ovulation; menstruation; placentation; intestinal adhesions; atherosclerosis; scleroderma; hypertrophic scars, i.e., keloids; cat scratch disease (Rochele minalia quintosa); and ulcers (Helobacter pylori). It should be noted that the assays described herein can identify compounds that affect endostatin gene activity by either affecting endostatin gene expression or by affecting the level of endostatin gene product activity. For example, compounds may be identified that are involved in another step in the pathway in which the endostatin gene and/or endostatin gene product is involved and, by affecting this same pathway may modulate the effect of endostatin on the development of an angiogenesis-related disorder such as cancer. Such compounds can be used as part of a therapeutic method for the treatment of the disorder.

Described below are cell-based and animal model-based assays for the identification of compounds exhibiting such an ability to ameliorate symptoms of an angiogenesis-related disorder, e.g., cancer.

First, cell-based systems can be used to identify compounds that may act to ameliorate symptoms of an angiogenesis-related disorder, e.g., cancer. Such cell systems can include, for example, recombinant or non-recombinant cell, such as cell lines, that express the endostatin gene.

In utilizing such cell systems, cells that express endostatin may be exposed to a compound suspected of exhibiting an ability to ameliorate symptoms of an angiogenesis-related disorder, e.g., cancer, at a sufficient concentration and for a sufficient time to elicit such an amelioration of such symptoms in the exposed cells. After exposure, the cells can be assayed to measure alterations in the expression of the endostatin gene, e.g., by assaying cell lysates for endostatin mRNA transcripts (e.g., by Northern analysis) or for endostatin gene products expressed by the cell; compounds that modulate expression of the endostatin gene are good candidates as therapeutics. Alternatively, the cells are examined to determine whether one or more cellular phenotypes associated with an angiogenesis-related disorder, e.g., cancer, has been altered to resemble a more normal or unimpaired, unaffected phenotype, or a phenotype more likely to produce a lower incidence or severity of disorder symptoms.

In addition, animal-based systems or models for an angiogenesis-related disorder, e.g., cancer, may be used to identify compounds capable of ameliorating symptoms of the disorder. Such animal-based systems or models may include, for example, transgenic mice, e.g., mice that have been genetically engineered to express exogenous or endogenous endostatin sequences or, alternatively, to no longer express endogenous endostatin gene sequences (i.e., "knock-out" mice). Such animal models may be used as test substrates for the identification of drugs, pharmaceuticals, therapies and interventions that may be effective in treating such disorders. For example, animal models may be exposed to a compound suspected of exhibiting an ability to ameliorate symptoms, at a sufficient concentration and for a sufficient time to elicit such an amelioration of symptoms of an angiogenesis-related disorder, e.g., cancer, in the exposed animals. The response of the animals to the exposure may be monitored by assessing the reversal of such symptoms.

With regard to intervention, any treatments that reverse any aspect of symptoms of an angiogenesis-related disorder, e.g., cancer, should be considered as candidates for human therapeutic intervention in such a disorder. Dosages of test agents may be determined by deriving dose-response curves, as discussed in, below.

A variety of methods can be employed for the diagnostic and prognostic evaluation of angiogenesis-related disorders, such as cancer, and for the identification of subjects having a predisposition to such disorders.

Such methods may, for example, utilize reagents such as the endostatin gene nucleotide sequences described above, and antibodies directed against endostatin gene products, including peptide fragments thereof, as described, above. Specifically, such reagents may be used, for example, for:

(1) the detection of the presence of endostatin gene mutations, or the detection of either over- or under-expression of endostatin gene mRNA relative to the state of an angiogenesis-related disorder, such as cancer;

(2) the detection of either an over- or an under-abundance of endostatin gene product relative to the unaffected state; and (3) the detection of an aberrant level of endostatin gene product activity relative to the unaffected state.

Endostatin gene nucleotide sequences can, for example, be used to diagnose an angiogenesis-related disorder using, for example, the techniques for endostatin mutation detection described above.

The methods described herein may be performed, for example, by utilizing pre-packaged diagnostic kits comprising at least one specific endostatin gene nucleic acid or anti-endostatin gene antibody reagent described herein, which may be conveniently used, e.g., in clinical settings, to diagnose subjects exhibiting abnormalities of an angiogenesis-related disorder, e.g., cancer.

For the detection of endostatin mutations, any nucleated cell can be used as a starting source for genomic nucleic acid. For the detection of endostatin gene expression or endostatin gene products, any cell type or tissue in which the endostatin gene is expressed may be utilized.

Nucleic acid-based detection techniques are described, above. Peptide detection techniques are described, above.

The methods described herein can furthermore be utilized as diagnostic or prognostic assays to identify subjects having or at risk of developing a disease or disorder associated with aberrant expression or activity of a polypeptide of the invention. For example, the assays described herein, such as the preceding diagnostic assays or the following assays, can be utilized to identify a subject having or at risk of developing a disorder associated with aberrant expression or activity of a polypeptide of the invention. Alternatively, the prognostic assays can be utilized to identify a subject having or at risk for developing such a disease or disorder. Thus, the present invention provides a method in which a test sample is obtained from a subject and a polypeptide or nucleic acid (e.g., mRNA, genomic DNA) of the invention is detected, wherein the presence of the polypeptide or nucleic acid is diagnostic for a subject having or at risk of developing a disease or disorder associated with aberrant expression or activity of the polypeptide. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a polypeptide of the invention. For example, such methods can be used to determine whether a subject can be effectively treated with a specific agent or class of agents (e.g., agents of a type which decrease activity of the polypeptide). Thus, the present invention provides methods for determining whether a subject can be effectively treated with an agent for a disorder associated with aberrant expression or activity of a polypeptide of the invention in which a test sample is obtained and the polypeptide or nucleic acid encoding the polypeptide is detected (e.g., wherein the presence of the polypeptide or nucleic acid is diagnostic for a subject that can be administered the agent to treat a disorder associated with aberrant expression or activity of the polypeptide).

The methods of the invention also can be used to detect genetic lesions or mutations in a gene of the invention, thereby determining if a subject with the lesioned gene is at risk for a disorder characterized aberrant expression or activity of a polypeptide of the invention. In preferred embodiments, the methods include detecting, in a sample of cells from the subject, the presence or absence of a genetic lesion or mutation characterized by at least one of an alteration affecting the integrity of a gene encoding the polypeptide of the invention, or the mis-expression of the gene encoding the polypeptide of the invention. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in a gene (see, e.g., Abravaya et al. (1995) *Nucleic Acids Res.* 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a selected gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotides probes (Cronin et al., 1996, Human Mutation 7:244–255; Kozal et al., 1996, Nature Medicine 2:753–759). For example, genetic mutations can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the selected gene and detect mutations by comparing the sequence of the sample nucleic acids with the corresponding wild-type (control) sequence. (Examples of sequencing reactions include those based on techniques developed by Maxim and Gilbert, 1977, Proc. Natl. Acad. Sci. USA 74:560 or Sanger, 1977, Proc. Natl. Acad. Sci. USA 74:5463). It is also contemplated that any of a variety of automated sequencing procedures can be utilized when performing the diagnostic assays (1995, Bio/Techniques 19:448), including sequencing by mass spectrometry (see, e.g., PCT Publication No. WO 94/16101; Cohen et al., 1996, Adv. Chromatogr. 36:127–162; and Griffin et al., 1993, Appl. Biochem. Biotechnol. 38:147–159).

Other methods for detecting mutations in a selected gene include methods in which protection from cleavage agents is used to detect mismatched bases in RNA/RNA or RNA/DNA heteroduplexes (Myers et al., 1985, Science 230:1242). In general, the technique of mismatch cleavage entails providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to basepair mismatches between the control and sample strands. RNA/DNA duplexes can be treated with RNase to digest mismatched regions, and DNA/DNA hybrids can be treated with S1 nuclease to digest mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. (See, e.g., Cotton et al., 1988, Proc. Natl. Acad. Sci. USA 85:4397; Saleeba et al., 1992, Methods Enzymol. 217:286–295.) In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair enzymes") in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al., 1994, Carcinogenesis 15:1657–1662). According to an exemplary embodiment, a probe based on a selected sequence, e.g., a wild-type sequence, is hybridized to a cDNA or other DNA product from a test cell(s). The duplex is treated with a DNA mismatch repair enzyme, and the cleavage products, if any, can be detected from electrophoresis protocols or the like. (See, e.g., U.S. Pat. No. 5,459,039.) In other embodiments, alterations in electrophoretic mobility will be used to identify mutations in genes. For example, SSCP may be used to detect differences in electrophoretic mobility between mutant and wild type nucleic acids (Orita et al., 1989, Proc. Natl. Acad. Sci. USA 86:2766; see also Cotton, 1993, Mutat. Res. 285:125–144; Hayashi, 1992, Genet. Anal. Tech. Appl. 9:73–79). Single-stranded DNA fragments of sample and control nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., 1991, Trends Genet. 7:5).

In yet another embodiment, the movement of mutant or wild-type fragments in polyacrylamide gels containing a gradient of denaturant is assayed using denaturing gradient gel electrophoresis (DGGE) (Myers et al., 1985, Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner, 1987, Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al., 1986, Nature 324:163; Saiki et al., 1989, Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al., 1989, Nucleic Acids Res. 17:2437–2448) or at the extreme 3' end of one primer where, under appropriate conditions, mismatch can prevent or reduce polymerase extension (Prossner, 1993, Tibtech 11:238). In addition, it may be desirable to introduce a novel restriction site in the region of the mutation to create cleavage-based detection (Gasparini et al., 1992, Mol. Cell Probes 6:1). It is anticipated that in certain embodiments amplification may also be performed using Taq ligase for amplification (Barany, 1991, Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose subjects exhibiting symptoms or family history of a disease or illness involving a gene encoding a polypeptide of the invention. Furthermore, any cell type or tissue, preferably peripheral blood leukocytes, in which the polypeptide of the invention is expressed may be utilized in the prognostic assays described herein.

The invention further provides kits that facilitate the use and/or detection of endostatin genes and gene products described herein. The kits described herein may be conveniently used, e.g., in clinical settings to diagnose subjects exhibiting symptoms or family history of a disease or illness involving a gene encoding a polypeptide of the invention. Furthermore, any cell type or tissue in which the polypeptide of the invention is expressed may be utilized in the prognostic assays described herein.

In one embodiment, a diagnostic test kit for identifying cells or tissues which mis-express endostatin genes or gene products is provided. In this embodiment, a diagnostic kit is provided, with one or more containers comprising an oligonucleotide, e.g., a detectably labeled oligonucleotide, which hybridizes to a nucleic acid sequence encoding a polypeptide of the invention. In another embodiment, a kit is provided, with one or more containers comprising a pair of primers useful for amplifying a nucleic acid molecule encoding a polypeptide of the invention. In various other embodiments, the kit can also comprise, e.g., a buffering agent, a preservative, or a protein stabilizing agent. The kit also can comprise components necessary for detecting the detectable agent (e.g., an enzyme or a substrate). The kit also can contain a control sample or a series of control samples which can be assayed and compared to the test sample. Each component of the kit is usually enclosed within an individual container and all of the various containers are within a single package along with instructions for observing whether the tested subject is suffering from, or is at risk of developing, a disorder associated with aberrant expression of the polypeptide. Such a kit can be used, for example, to measure the levels of a nucleic acid molecule encoding the protein in a sample of cells from a subject, e.g., detecting mRNA levels or determining whether a gene encoding the protein has been mutated or deleted.

In another embodiment, the invention provides kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention as discussed, for example, in sections above relating to uses of the sequences of the invention. In this embodiment, a kit is provided, with one or more containers comprising: (1) a first antibody (e.g., attached to a solid support) which binds to a polypeptide of the invention; and, optionally, (2) a second, different antibody which binds to either the polypeptide or the first antibody and is conjugated to a detectable agent. Such kits can be used to determine if a subject is suffering from, or is at increased risk of, an angiogenesis-related disorder, such as cancer.

Described below are methods and compositions whereby an endostatin-mediated process can be modulated and/or whereby an angiogenesis-related disorder, e.g., cancer, may be treated.

For example, such methods can comprise administering compounds which modulate the expression of an endostatin gene and/or the synthesis or activity of an endostatin gene product so that the process is modulated or a symptom of the disorder is ameliorated.

Alternatively, in those instances whereby the angiogenesis-related disorder, e.g., cancer, results from endostatin gene mutations that lower or abolish endostatin activity, respectively, such methods can comprise supplying a mammal with a nucleic acid molecule encoding an unimpaired endostatin gene product such that an unimpaired endostatin gene product is expressed and symptoms of the disorder are ameliorated.

In another embodiment of methods for the treatment of mammalian angiogenesis-related disorder, e.g., cancer, resulting from endostatin gene mutations, such methods can comprise supplying a mammal with a cell comprising a nucleic acid molecule that encodes an unimpaired endostatin gene product such that the cell expresses the unimpaired endostatin gene product and symptoms of the disorder are ameliorated.

In cases in which a loss of normal endostatin gene product function results in the development of an angiogenesis-related disorder phenotype, e.g., cancer, an increase in endostatin gene product activity would facilitate progress towards an asymptomatic state in individual organisms exhibiting a deficient level of endostatin gene expression and/or endostatin gene product activity. Methods for enhancing the expression or synthesis of endostatin can include, for example, methods such as those described below.

Alternatively, symptoms of angiogenesis-related disorder phenotype, e.g., cancer, may be ameliorated by administering a compound that decreases the level of endostatin gene expression and/or endostatin gene product activity. Methods for inhibiting or reducing the level of endostatin synthesis or expression can include, for example, methods such as those described below.

In one embodiment of treatment methods, the compounds administered do not comprise compounds, in particular drugs, reported to ameliorate or exacerbate the symptoms of an angiogenesis-related disorder. If such treatment methods do comprise such compounds, preferably such compounds are utilized in a manner (e.g., different dosage, mode of administration, and/or co-administration with one or more additional compounds) that differs from the manner in which such compounds have been administered previously.

In another embodiment, symptoms of a disorder described herein, e.g., cancer, may be ameliorated by endostatin protein therapy methods, e.g., decreasing or increasing the level and/or activity of endostatin using the endostatin protein, fusion protein, and peptide sequences described above, or by the administration of proteins or protein fragments (e.g., peptides) which interact with an endostatin gene or gene product and thereby inhibit or potentiate its activity.

Such protein therapy may include, for example, the administration of a functional endostatin protein or fragments of an endostatin protein (e.g., peptides) which represent functional endostatin domains.

In one embodiment, endostatin fragments or peptides representing a functional endostatin binding domain are administered to an individual organism such that the peptides bind to an endostatin binding protein, e.g., an endostatin receptor. Such fragments or peptides may serve to inhibit endostatin activity in an individual organism by competing with, and thereby inhibiting, binding of endostatin to the binding protein, thereby ameliorating symptoms of a disorder described herein. Alternatively, such fragments or peptides may enhance endostatin activity in an individual organism by mimicking the function of endostatin in vivo, thereby ameliorating the symptoms of a disorder described herein.

The proteins and peptides which may be used in the methods of the invention include synthetic (e.g., recombinant or chemically synthesized) proteins and peptides, as well as naturally occurring proteins and peptides. The proteins and peptides may have both naturally occurring and non-naturally occurring amino acid residues (e.g., D-amino acid residues) and/or one or more non-peptide bonds (e.g., imino, ester, hydrazide, semicarbazide, and azo bonds). The proteins or peptides may also contain additional chemical groups (i.e., functional groups) present at the amino and/or carboxy termini, such that, for example, the stability, bioavailability, and/or inhibitory activity of the peptide is enhanced. Exemplary functional groups include hydrophobic groups (e.g. carbobenzoxyl, dansyl, and t-butyloxycarbonyl, groups), an acetyl group, a 9-fluorenylmethoxy-carbonyl group, and macromolecular carrier groups (e.g., lipid-fatty acid conjugates, polyethylene glycol, or carbohydrates) including peptide groups.

In another embodiment, symptoms of certain angiogenesis-related disorders, such as cancer, may be ameliorated by decreasing the level of endostatin gene expression and/or endostatin gene product activity by using endostatin gene sequences in conjunction with well-known antisense, gene "knock-out," ribozyme and/or triple helix methods to decrease the level of endostatin gene expression. Among the compounds that may exhibit the ability to modulate the activity, expression or synthesis of the endostatin gene, including the ability to ameliorate the symptoms of an angiogenesis-related disorder, e.g., cancer, are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the endostatin gene could be used in an antisense approach to inhibit translation of endogenous endostatin mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S.A. 86, 6553–6556; Lemaitre, et al., 1987, Proc. Natl. Acad. Sci. 84, 648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6, 958–976) or intercalating agents (see, e.g., Zon, 1988, Pharm. Res. 5, 539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2- thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987, Nucl. Acids Res. 15, 6625–6641). The oligonucleotide is a 2'-0-methylribonucleotide (Inoue, et al., 1987, Nucl. Acids Res. 15, 6131–6148), or a chimeric RNA-DNA analogue (Inoue, et al., 1987, FEBS Lett. 215, 327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16, 3209), methylphosphonate oligonucleotides can be prepared by use of controlled pore glass polymer supports (Sarin, et al., 1988, Proc. Natl. Acad. Sci. U.S.A. 85, 7448–7451), etc.

While antisense nucleotides complementary to the target gene coding region sequence could be used, those complementary to the transcribed, untranslated region are most preferred.

Antisense molecules should be delivered to cells that express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the subject will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Benoist and Chambon, 1981, Nature 290, 304–310), the promoter contained in the 3' long terminal repeat of Rous sarcoma virus (Yamamoto, et al., 1980, Cell 22, 787–797), the herpes thymidine kinase promoter (Wagner, et al., 1981, Proc. Natl. Acad. Sci. U.S.A. 78, 1441–1445), the regulatory sequences of the metallothionein gene (Brinster, et al., 1982, Nature 296, 39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver, et al., 1990, Science 247, 1222–1225).

Ribozymes are enzymatic RNA molecules capable of catalyzing the specific cleavage of RNA. (For a review, see Rossi, 1994, Current Biology 4, 469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology*: A *Comprehensive Desk Reference*, VCH Publishers, New York, (see especially FIG. 4, page 833) and in Haseloff and Gerlach, 1988, Nature, 334, 585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug, et al, 1984, Science, 224, 574–578; Zaug and Cech, 1986, Science, 231, 470–475; Zaug, et al., 1986, Nature, 324, 429–433; published International patent application No. WO 88/04300 by University Patents Inc.; Been and Cech, 1986, Cell, 47, 207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes, unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, Nature 317, 230–234; Thomas and Capecchi, 1987, Cell 51, 503–512; Thompson, et al., 1989, Cell 5, 313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6), 569–584; Helene, et al., 1992, Ann. N.Y. Acad. Sci., 660, 27–36; and Maher, 1992, Bioassays 14(12), 807–815).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyri-bonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

With respect to an increase in the level of normal endostatin gene expression and/or endostatin gene product activity, endostatin gene nucleic acid sequences, described above, for example, can be utilized for the treatment of an angiogenesis-related disorder, e.g., cancer. Such treatment can be administered, for example, in the form of gene replacement therapy. Specifically, one or more copies of a normal endostatin gene or a portion of the endostatin gene that directs the production of a endostatin gene product exhibiting normal endostatin gene function, may be inserted into the appropriate cells within a subject, using vectors that include, but are not limited to, adenovirus, adeno-associated virus, herpesvirus and retrovirus vectors, in addition to other particles that introduce DNA into cells, such as liposomes.

Because endostatin genes can be expressed in the brain, such gene replacement therapy techniques should be capable delivering endostatin gene sequences to these cell types within subjects. Thus, in one embodiment, techniques that are well known to those of skill in the art (see, e.g., PCT Publication No. WO 89/10134, published Apr. 25, 1988) can be used to enable endostatin gene sequences to cross the blood-brain barrier readily and to deliver the sequences to cells in the brain. With respect to delivery that is capable of crossing the blood-brain barrier, viral vectors such as, for example, those described above, are preferable.

In another embodiment, techniques for delivery involve direct administration of such endostatin gene sequences to the site of the cells in which the endostatin gene sequences are to be expressed.

Additional methods that may be utilized to increase the overall level of endostatin gene expression and/or endostatin gene product activity include the introduction of appropriate endostatin-expressing cells, preferably autologous cells, into a subject at positions and in numbers that are sufficient to ameliorate the symptoms of an angiogenesis-related disorder, e.g., cancer. Such cells may be either recombinant or non-recombinant.

Among the cells that can be administered to increase the overall level of endostatin gene expression in a subject are normal cells, preferably liver cells, that express the endostatin gene.

Alternatively, cells, preferably autologous cells, can be engineered to express endostatin gene sequences, and may then be introduced into a subject in positions appropriate for the amelioration of the symptoms of an angiogenesis-related disorder, e.g., cancer. Alternately, cells that express an unimpaired endostatin gene and that are from an MHC matched individual organism can be utilized, and may include, for example, liver cells. The expression of the endostatin gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described above, that are capable of modulating endostatin gene product activity can be administered using standard techniques that are well known to those of skill in the art. In instances in which the compounds to be administered are to involve an interaction with brain cells, the administration techniques should include well known ones that allow for a crossing of the blood-brain barrier.

Agents, or modulators, which have a stimulatory or inhibitory effect on activity or expression of a polypeptide of the invention as identified by a screening assay described herein can be administered to individual organisms to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual organism may be considered. Differences in metabolism of therapeutics can lead to severe toxicity or therapeutic failure by altering the relation between dose and blood concentration of the pharmacologically active drug. Thus, the pharmacogenomics of the individual organism permits the selection of effective agents (e.g., drugs) for prophylactic or therapeutic treatments based on a consideration of the individual organism's genotype. Such pharmacogenomics can further be used to determine appropriate dosages and therapeutic regimens. Accordingly, the activity of a polypeptide of the invention, expression of a nucleic acid of the invention, or mutation content of a gene of the invention in an individual organism can be determined to thereby select appropriate agent(s) for therapeutic or prophylactic treatment of the individual organism.

Pharmacogenomics deals with clinically significant hereditary variations in the response to drugs due to altered drug disposition and abnormal action in affected individual organisms. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some subjects do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a polypeptide of the invention, expression of a nucleic acid encoding the polypeptide, or mutation content of a gene encoding the polypeptide in an individual organism can be determined to thereby select appropriate agent(s) for therapeutic or prophylactic treatment of the individual organism. In addition, pharmacogenetic studies can be used to apply genotyping of polymorphic alleles encoding drug-metabolizing enzymes to the identification of an individual organism's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

Monitoring the influence of agents (e.g., drugs, compounds) on the expression or activity of a polypeptide of the invention (e.g., the ability to modulate aberrant cell proliferation chemotaxis, and/or differentiation) can be applied not only in basic drug screening, but also in clinical trials. For example, the effectiveness of an agent, as determined by a screening assay as described herein, to increase gene expression, protein levels or protein activity, can be monitored in clinical trials of subjects exhibiting decreased gene expression, protein levels, or protein activity. Alternatively, the effectiveness of an agent, as determined by a screening assay, to decrease gene expression, protein levels or protein activity, can be monitored in clinical trials of subjects exhibiting increased gene expression, protein levels, or protein activity. In such clinical trials, expression or activity of a polypeptide of the invention and preferably, that of other polypeptide that have been implicated in for example, a cellular proliferation disorder, can be used as a marker of the immune responsiveness of a particular cell.

For example, and not by way of limitation, genes, including those of the invention, that are modulated in cells by treatment with an agent (e.g., compound, drug or small molecule) which modulates activity or expression of a polypeptide of the invention (e.g., as identified in a screening assay described herein) can be identified. Thus, to study the effect of agents on cellular proliferation disorders, for example, in a clinical trial, cells can be isolated and RNA prepared and analyzed for the levels of expression of a gene of the invention and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of a gene of the invention or other genes. In this way, the gene expression pattern can serve as a marker, indicative of the physiological response of the cells to the agent. Accordingly, this response state may be determined before, and at various points during, treatment of the individual organism with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of the polypeptide or nucleic acid of the invention in the preadministration sample; (iii) obtaining one or more post-administration samples from the subject; (iv) detecting the level the of the polypeptide or nucleic acid of the invention in the post-administration samples; (v) comparing the level of the polypeptide or nucleic acid of the invention in the pre-administration sample with the level of the polypeptide or nucleic acid of the invention in the post-administration sample or samples; and (vi) altering the administration of the agent to the subject accordingly. For example, increased administration of the agent may be desirable to increase the expression or activity of the polypeptide to higher levels than detected, i.e., to increase the effectiveness of the agent. Alternatively, decreased administration of the agent may be desirable to decrease expression or activity of the polypeptide to lower levels than detected, i.e., to decrease the effectiveness of the agent.

The compounds of this invention can be formulated and administered to inhibit a variety of angiogenesis-related disorders by any means that produces contact of the active ingredient with the agents site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a therapeutically effective amount of the compound sufficient to result in amelioration of symptoms of the angiogenesis-related disorder and will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50 /ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Specific dosages may also be utilized for antibodies. Typically, the preferred dosage is 0.1 mg/kg to 100 mg/kg of body weight (generally 10 mg/kg to 20 mg/kg), and if the antibody is to act in the brain, a dosage of 50 mg/kg to 100 mg/kg is usually appropriate. If the antibody is partially human or fully human, it generally will have a longer half-life within the human body than other antibodies. Accordingly, lower dosages of partially human and fully human antibodies is often possible. Additional modifications may be used to further stabilize antibodies. For example, lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

A therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weigh Moreover, treatment of a subject with a therapeutically effective amount of a protein, polypeptide or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5 or 6 weeks.

The present invention further encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors known to those or ordinary skill in the art, e.g., a physician. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release.

Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Useful pharmaceutical dosage forms, for administration of the compounds of this invention can be illustrated as follows:

Capsules: Capsules are prepared by filling standard two-piece hard gelatin capsulates each with the desired amount of powdered active ingredient, 175 milligrams of lactose, 24 milligrams of talc and 6 milligrams magnesium stearate.

Soft Gelatin Capsules: A mixture of active ingredient in soybean oil is prepared and injected by means of a positive displacement pump into gelatin to form soft gelatin capsules containing the desired amount of the active ingredient. The capsules are then washed and dried.

Tablets: Tablets are prepared by conventional procedures so that the dosage unit is the desired amount of active ingredient. 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption.

Injectable: A parenteral composition suitable for administration by injection is prepared by stirring 1.5% by weight of active ingredients in 10% by volume propylene glycol and water. The solution is made isotonic with sodium chloride and sterilized.

Suspension: An aqueous suspension is prepared for oral administration so that each 5 millimeters contain 100 milligrams of finely divided active ingredient, 200 milligrams of sodium carboxymethyl cellulose, 5 milligrams of sodium benzoate, 1.0 grams of sorbitol solution U.S.P. and 0.025 millimeters of vanillin.

Gene Therapy Administration: Where appropriate, the gene therapy vectors can be formulated into preparations in solid, semisolid, liquid or gaseous forms such as tablets, capsules, powders, granules, ointments, solutions, suppositones, injections, inhalants, and aerosols, in the usual ways for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions can be used alone or in appropriate association, as well as in combination, with other pharmaceutically active compounds.

Accordingly, the pharmaceutical composition of the present invention may be delivered via various routes and to various sites in an animal body to achieve a particular effect (see, e.g., Rosenfeld et al. (1991), supra; Rosenfeld et al., Clin. Res., 3 9(2), 31 1A (1991 a); Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The compositions of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and animal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

Accordingly, the present invention also provides a method of transferring a therapeutic gene to a host, which comprises administering the vector of the present invention, preferably as part of a composition, using any of the aforementioned routes of administration or alternative routes known to those skilled in the art and appropriate for a particular application. The "effective amount" of the composition is such as to produce the desired effect in a host which can be monitored using several end-points known to those skilled in the art. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer).

These methods described herein are by no means all-inclusive, and further methods to suit the specific application will be apparent to the ordinary skilled artisan. Moreover, the effective amount of the compositions can be further approximated through analogy to compounds known to exert the desired effect.

Furthermore, the actual dose and schedule can vary depending on whether the compositions are administered in combination with other pharmaceutical compositions, or depending on individual differences in pharmacokinetics, drug disposition, and metabolism. Similarly, amounts can vary in in vitro applications depending on the particular cell line utilized (e.g., based on the number of adenoviral receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

The following examples are offered by way of example, and are not intended to limit the scope of the invention in any manner.

EXAMPLES

Identification and Cloning of Endostatin Genes

In the Example presented in this section, studies are described that identify novel canine genes, referred to herein as endostatin, which are involved in angiogenesis-related disorders, e.g., cancer.

Materials and Methods

1. Isolation of RNA from dog liver tissue. 50 mg of dog liver tissue was disrupted and homogenized by rotor-stator homogenizer (Kontes, Vineland, N.J.) and total RNA was purified using Rneasy Mini Kit following instructions from manufacturer (Qiagen Inc., Santa Clarita, Calif.). 30 $\mu$g of RNA was isolated and was suspended in H20 at 0.5 $\mu$g/$\mu$l.

2. RT-PCR amplification and cloning of a region of canine collagen XVIII encompassing endostatin. Endostatin is a C-terminal fragment of collagen XVIII (amino acid H1132-K1315 in murine collagen XVIII). A pair of primers were designed to amplify a region of canine collagen XVIII cDNA based on consensus sequences from human (Accession No. L22548), mouse (Accession No. U03714) and chicken (Accession No. AF083440). The 5' primer: CCCTGGCGGGCAGATGACATCCTGGCC (SEQ ID NO:5) corresponding to nucleotide #766–792 of murine partial collagen XVIII cDNA the 3' primer: CTCTTTGGCT-TCCTTTTATTCTTGAGGATTACAT (SEQ ID NO:6), corresponding to nucleotide #1569-1603 of murine partial collagen XVIII cDNA were used for the amplification reaction. The RT-PCR reaction was performed using Titan One Tube RT-PCR Kit from Boehringer Mannheim GmbH (Germany). 0.5 ug of dog liver RNA was denatured at 68° C. for 2 minutes. The reverse transcription reaction was performed at 50° C. for 30 minutes, and the PCR program was: hold at 94° C. for 3 minutes, followed by 35 cycles of 30 seconds at 94° C., 30 seconds at 55° C., 1.5 minutes at 68° C. and 5 minutes of extension at 68° C. The PCR products were analyzed by electrophoresis.

The PCR products were cloned into Eukaryotic TA cloning vector pCR 3.1 (Invitrogen, Carlsbad, Calif.) following manufacturer's instructions and designated as pCR3. 1-pro-ca-endostatin (pCR3.1 E:UC25432), deposited with the American Type Culture Collection (ATCC), Manassas, Va. 20110–2209, USA under Patent Deposit Designation PTA 2096. Three independent clones containing inserts of the expected size (0.8 kb) were sequenced (Advanced Genetic Analysis Center, St. Paul, Minn.). The sequences were assembled and analyzed using DNAStar (DNAStar Inc. Madison, Wis.).

3. Subcloning of HA-tapped canine endostatin. The exact fragment of canine collagen XVIII corresponding to endostatin was subcloned into pDisplay vector by RT-PCR amplification of dog liver RNA using primers: 5' primer-CTAGAGATCTCACACCCACCAGGACTTCCAGC, (SEQ ID NO: 14) 3' primer-CGTAGTCGACCTACTTGGAGAAGGAGGT-CATGACCGTAGTCG CCTACTTGGAGMGGAGGT-CATGAC (SEQ ID NO: 15). To facilitate don ng, two restriction enzyme sites Bgl II (5' primer) and Sal I (3' primer) were incorporated into the primer sequences as shown by underline. The insert was fused in-frame to the signal peptide and HA epitope sequences present in the vector. The stop codon TAG (shown in bold) of endostatin was included in the 3' primer to terminate translation, therefore the vector-encoded PDGFR transmembrane domain downstream of the insert would not be translated in the final plasmid construct, p Display-HA-ca-endostatin (PdisplayE:UC25433), deposited with the ATCC under Patent Deposit Designation PTA-2097.

4. Subcloning of canine endostatin (without HA tag). Canine endostatin was subcloned into pSecTag2 B vector by RT-PCR amplification of dog liver RNA using primers: 5' primer-GATTAAGCTTCACACCCACCAGG ACTTC-CAGCT (SEQ ID NO:7), 3' primer-CTGA <u>GAATTC</u>CTACTTGGAGAAGGAGGTCATGAC (SEQ ID NO:8). To facilitate cloning, two restriction enzyme sites Hind III (5' primer) and EcoR I (3' primer) were incorporated into the primer sequences as shown by underline. The insert was fused in-frame to the signal peptide sequences present in the vector. The stop codon TAG (shown in bold) of endostatin was included in the 3' primer to terminate translation. The final plasmid construct was designated pSecTag2-ca-endostatin (pSecTag2E:UC 25434) deposited with the ATCC under Patent Deposit Designation PTA-2098.

5. Cloning of murine endostatin. In order to compare the anti-angiogenesis activity of cloned canine endostatin to that of its murine counterpart, cDNAs encoding murine endostatin were RT-PCR amplified from mouse liver RNA and cloned into pDisplay vector. The primers used for amplifying murine endostatin were: 5'-CTAG <u>AGATCT</u>CATACTCATCAGGACTTTCAGC (SEQ ID NO:9), 3'-GCTA<u>GTCGAC</u>CTATTTGGAGAAAGAGGT-CATG (SEQ ID NO:10). The flanking restriction sites Bgl II (5' primer) and Sal 1 (3' primer) are underlined and the stop codon is shown in bold. The resultant plasmid was designated as pDisplay-HA-mu-endostatin (Accession No. U03714).

Results

The cDNAs encoding a fragment of canine collagen XVIII which contains the coding region of endostatin were amplified by RT-PCR from dog liver mRNA using primers designed from consensus sequences from several species. The nucleotide sequence of pro-endostatin is shown in FIG. 2(SEQ ID NO:1), and the predicted amino acid sequence is shown in FIG. 3(SEQ ID NO:2). The region corresponding to endostatin based on homology is in bold in FIG. 3 and the exact nucleotide sequence and predicated amino acid sequence of canine endostatin (184 amino acids) is shown in FIG. 4(SEQ ID NO:3) and FIG. 5(SEQ ID NO:4) respectively. FIG. 6 shows the alignment of all known amino acid sequences of endostatin, and the degree of homology between canine endostatin and that of human, mouse and chicken is 84%, 83% and 76% respectively.

Expression of Endostatin Genes

In the Example presented in this section, studies are described that identify methods to express and assay the novel canine endostatin genes.

Materials and Methods

1. Transfection of endostatin. Human 293 cells grown in 6 well plate were transfected with 2.5 ug of plasmids encoding canine or murine endostatin using CalPhos Mammalian Transfection Kit (CLONTECH Laboratories, Inc., Palo Alto, Calif.).

2. Detection of endostatin by immunofluorescence. 2 days post-transfection, cells were fixed in 4% paraformaldehyde, permeablized in 0.05% Triton X100, and blocked in 1% goat serum (all chemicals from Sigma, St. Louis, Mo.). HA.11 (BabCO, Richmond, Calif.), a monoclonal antibody against HA epitope was used at 1:500 dilution to stain the cells, and TR1TC conjugated anti-mouse IgG (Sigma) was used at 1:1,000 for detection. The immunofluorescent cells were visualized under Nikon TE 300 microscope.

3. Detection of endostatin by immunoblot analysis. 2 days post-transfection, cells were harvested by lysis in Tris-Glycine SDS Sample Buffer (NOVEX, San Diego, Calif.). The culture supernatants were harvested by centrifugation at 3000 rpm for 15 minutes. The proteins were separated by 4–20% SDS-PAGE and transferred to PVDF membrane (NOVEX, San Diego, Calif.). For immunoblot analysis, HA antibody against HA epitope were diluted 1:500 and incubated with the blot for 1.5 hours. After incubating for 30 minutes with alkaline phosphatase conjugated anti-mouse IgG (1:10,00, Boehringer Mannheim, Indianapolis, Ind.), the bound antibody was detected using phosphatase substrate BCIP/NBT (KPL, Gaithersburg, Md.).

4. Endothelial cell proliferation assay. The anti-proliferative effect of cloned canine endostatin was tested using bovine pulmonary artery endothelial cells (C-PAE, ATCC, Manassas, Va.). The cells (104 cells/well) were plated in 24-well collagen I-coated plates (Collaborative Biomedical Products, Bedford, Mass.) in OptiMEM (GIBCO BRL, Rockville, Md.) with 2% fetal bovine serum (Nova-Tech Inc., Grand Island, Nebr.).

5. After 24 hour incubation, the medium was replaced with conditioned medium from transfected 293 cells supplemented with 1 ng/ml bFGF (Collaborative Biomedical Products, Bedford, Mass.). The cells were trypsinized 48 hours later and viable cells were counted using trypan blue staining and hemacytometer. The results were analyzed using Prizm 2.01 (Graphpad Software Inc., San Diego, Calif.).

Results

Figure 7:
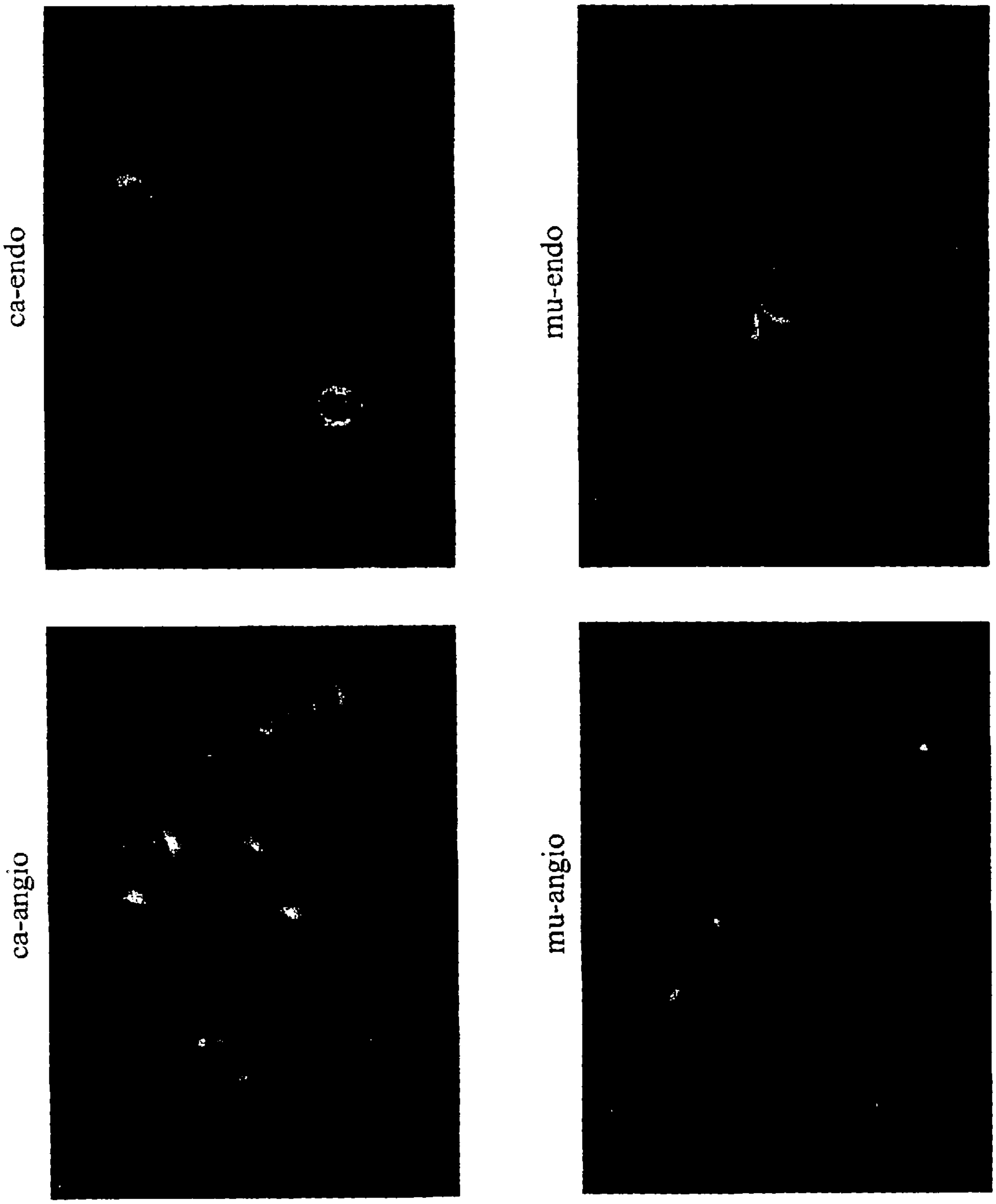
FIG. 7: Immunofluorescence analysis of canine and murine endostatin. 293 cells were transfected with HA-tagged canine endostatin (ca-endo) and murine endostatin (mu-endo). The cells were stained with antibody against the HA epitope and TRITC conjugated secondary antibody.

Expression of canine endostatin. The cDNAs encoding canine endostatin were subcloned into mammalian expression vector pDisplay. Because endostatin is a fragment of a secreted protein and normally circulates in the blood, the proteins were fused in-frame at the N-terminus to the murine Ig k-chain leader sequence which directs the protein to the secretory pathway, followed by fusion to hemagglutinin A epitope tag (HA) which allows for detection of expressed protein. Human 293 cells were transfected with plasmids encoding signal sequence and HA-tagged endostatin from dog and mouse, the cells were harvested 48 hours post transfection for analysis. FIG. 7 shows the results of immunofluorescent assay. The staining patterns of endostatin are characteristic of perinuclear endoplasmic reticulum and trans-Golgi, consistent with the notion that this protein is directed to the secretory pathway.

Figure 8:
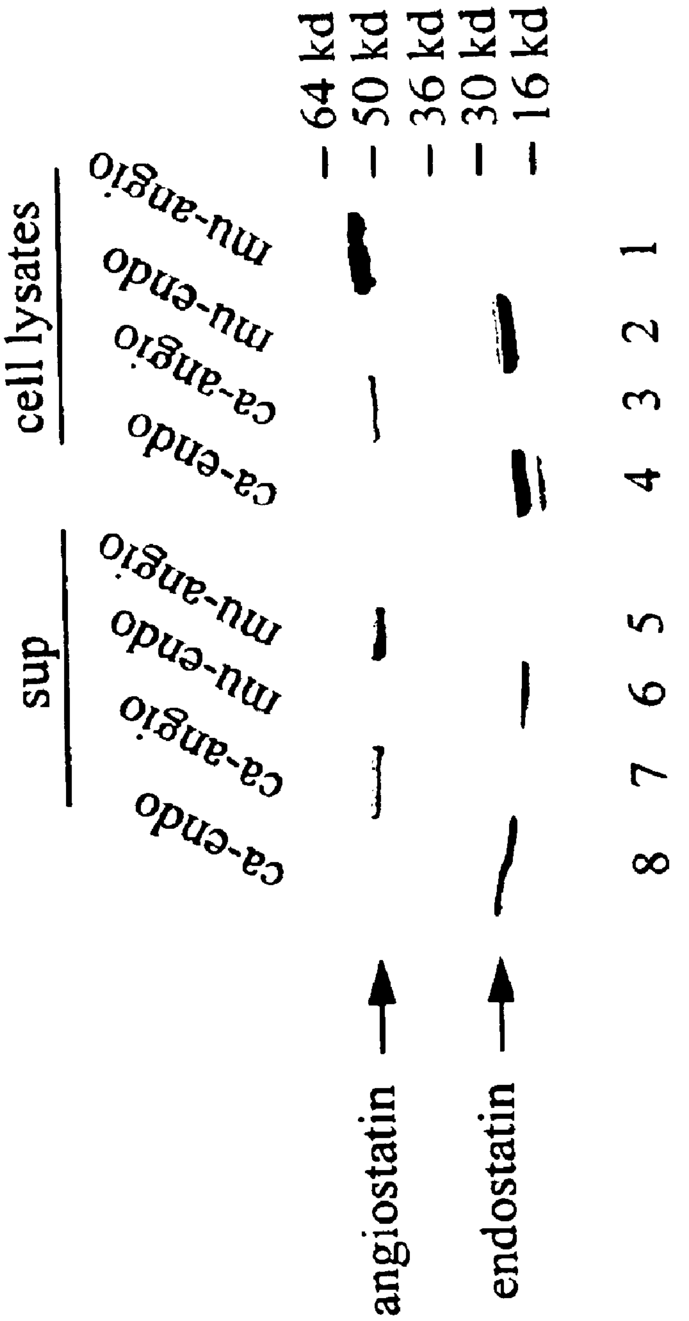
FIG. 8: Immunoblot analysis of 293 cells transfected with HA-tagged canine endostatin (ca-endo) and murine endostatin (mu-endo). Intracellular proteins from cell lysates and secreted proteins from culture supernatants (sup) were run on SDS-PAGE and analyzed by immunoblot using HA antibody and alkaline phosphatase conjugated secondary antibody.

1. The expression of endostatin was further studied by immunoblot analysis. The expression of transfected endostatin was detected from both cell lysates (FIG. 8, lane 2 and 4) and culture supernatants (FIG. 8, lane 6 and 8). Several forms of intracellular endostatin with molecular weights ranging 20–25 kDa (FIG. 8, lane 2 and 4) exist. These are likely intermediates of protein maturation since only one discrete band was seen in the secreted form.

Figure 9:
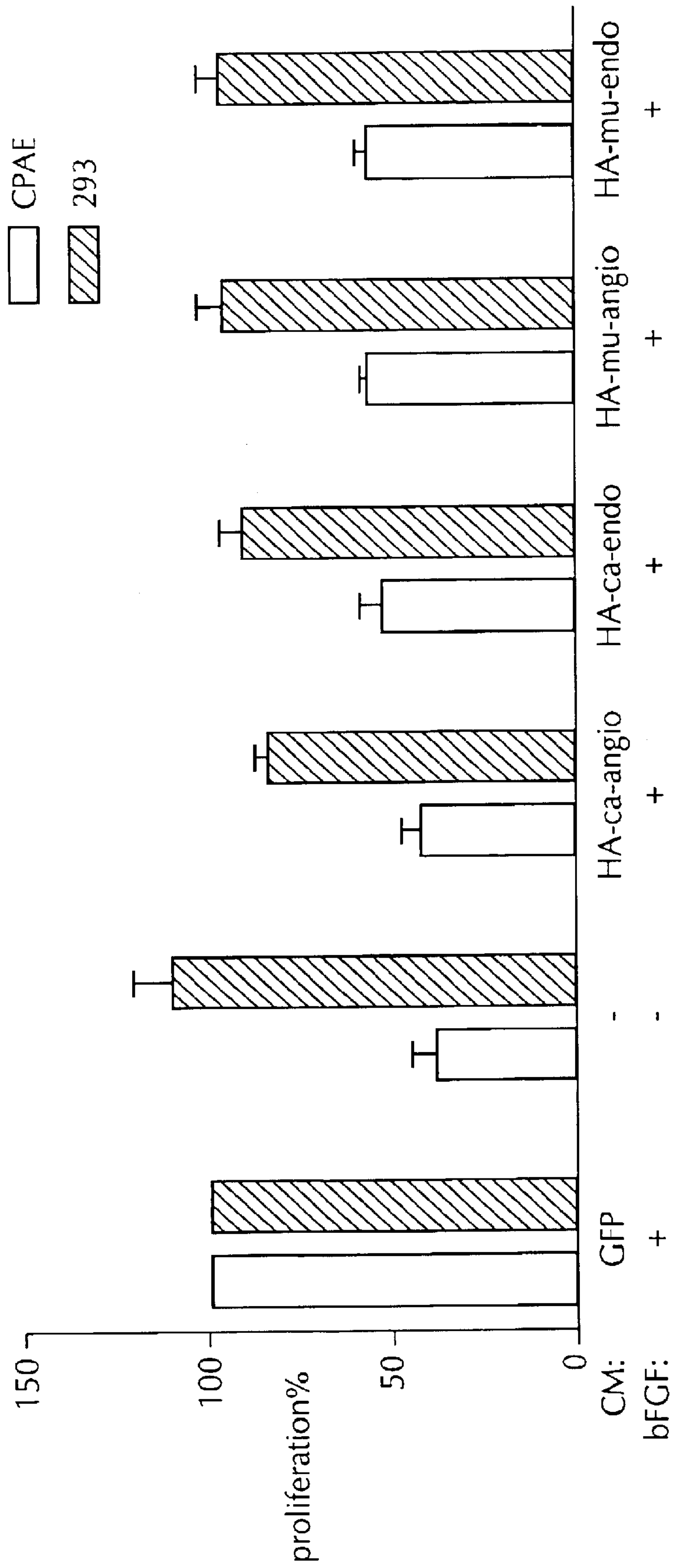
FIG. 9: Endothelial Cell Proliferation Assay. The figure shows a summary of inhibition of endothelial cell proliferation by HA-tagged canine endostatin (HA-ca-endo) and murine endostatin (HA-mu-endo). 293 cells were transfected with angiogenesis inhibitors or green fluorescent protein (GFP) as control. The supernatants were harvested 48 hours post transfection and incubated with bFGF stimulated CPAE bovine endothelial cells or 293 cells for 72 hours. The total numbers of cells were counted and plotted. Four independent experiments were carried out and each experiment was done in duplicate.
Figure 10:
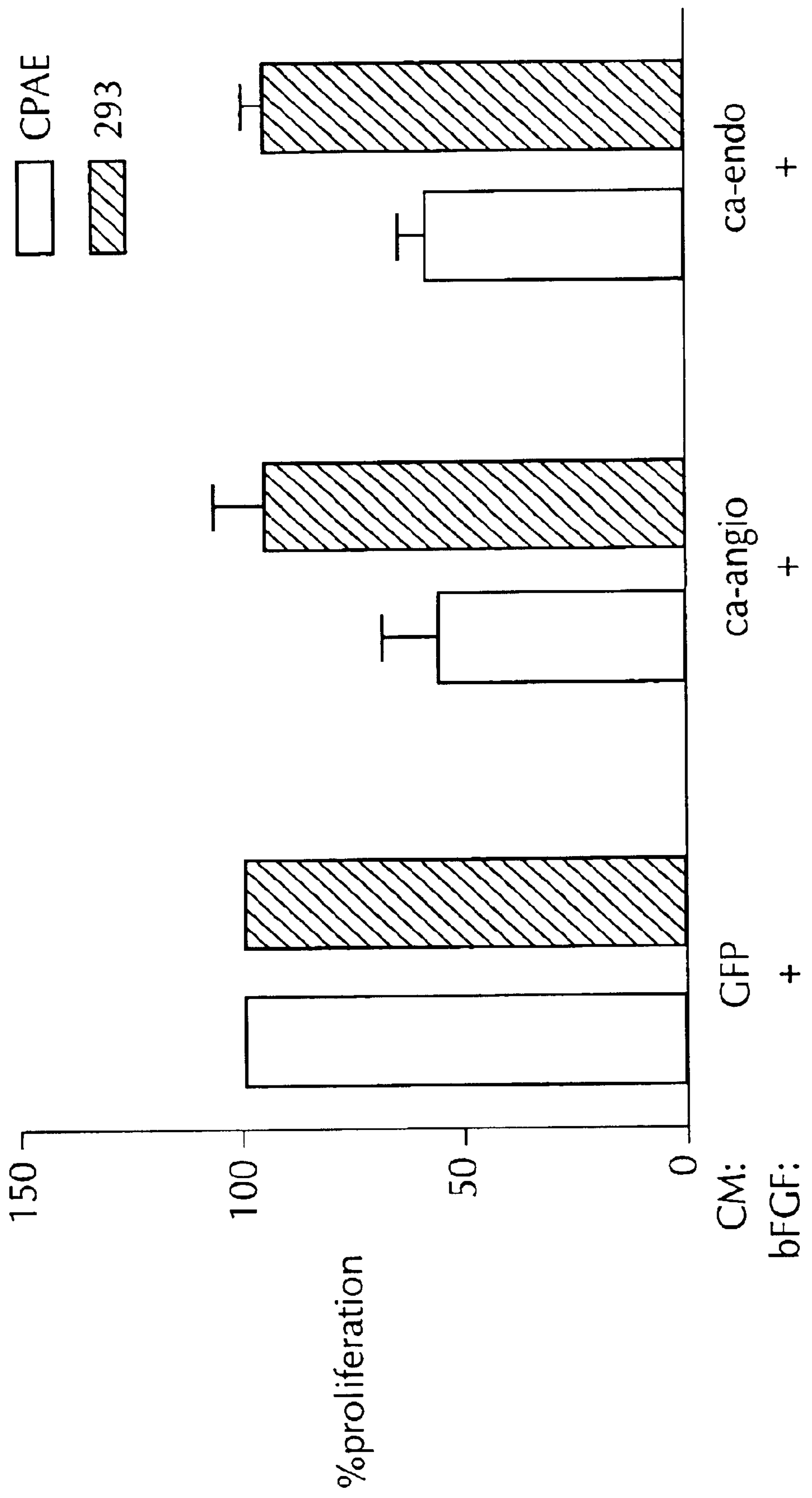
FIG. 10: Endothelial Cell Proliferation Assay. The figure shows a summary of inhibition of endothelial cell proliferation by untagged canine endostatin (ca-endo). 293 cells were transfected with angiogenesis inhibitors or green fluorescent protein (GFP) as control. The supernatants were harvested 48 hours post transfection and incubated with bFGF stimulated CPAE bovine endothelial cells or 293 cells for 72 hours. The total numbers of cells were counted and plotted. Three independent experiments were carried out and each experiment was done in duplicate.

2. Inhibition of endothelial cell proliferation. One unique feature of endostatin is its ability to specifically inhibit endothelial cell proliferation (0□ Reilly et al., 1997, *Cell* 88(2):277–85; O□Reilly et al., 1994, Cell 79(2):3 15–28). Bovine pulmonary artery end cells (CPAE cells) (Dhanabal et al., 1999) were stimulated with basic fibroblast growth factor (bFGF) in the presence or absence of endostatin proteins produced from conditioned media from transfected 293 cells. The proliferation rate was normalized against control cells which were treated with bFGF and conditioned media from green fluorescent protein (GFP) transfected cells. The results from four independent experiments were summarized in FIG. 9. CPAE cells proliferated slowly without bFGF activation (38% of that of control). The addition of HA-tagged canine endostatin inhibited the stimulating effect of bFGF with CPAE cells proliferating at 53% of that of control respectively. The inhibitory activity seen with HA-tagged canine endostatin was comparable to that with the murine proteins (both at 57% level of controls). The differences in proliferation rate between control and each treated group were all statistically significant ($P<0.05$). In contrast, treatment with endostatin did not inhibit proliferation of the epithelial 293 cells, suggesting that the inhibitory effect of endostatin is specific to endothelial cells. Similar results were obtained using untagged canine endostatin (FIG. 10). The addition of canine endostatin specifically inhibited the stimulating effect of bFGF with CPAE cells proliferating at 59% of that of control. The differences in the proliferation rate between control and each treated group were all statistically significant ($P<0.005$, $n=3$).

Discussion

Here the cloning of the canine angiogenesis inhibitor endostatin is reported. It shares approximately 80% homology with its human and murine counterparts. To facilitate secretion of cloned proteins, a signal sequence from mouse Ig k-chain was fused to the N-terminus of endostatin. Immunofluorescent studies and immunoblot assays confirmed that the proteins were localized to the secretory pathway and secreted into conditioned media. Canine endostatin was also shown to specifically inhibit endothelial cell proliferation at a level comparable to its murine counterpart.

Mouse endostatin has been shown to inhibit the growth of a wide variety of primary and metastatic tumors. Furthermore, the treatment with endostatin can be repeated many times without inducing drug resistance or side effects. Since these angiogenesis inhibitors are directed at a novel target (endothelial cells), they can also be conveniently combined with other cancer therapies such as surgery, chemotherapy, radiation therapy and immunotherapy to achieve superior therapeutic effects. These properties have made endostatin a very attractive candidate for treating canine cancers, where a safe, efficacious, and broad-spectrum therapy is very much in need. However, the successful application of endostatin as a cancer therapy probably will involve repeated, continuing treatment in order to achieve long-term tumor suppression and dormancy (Boehm et al., 1997, Nature 390(6658):404–407). The cloning and identification of canine endostatin allows for the treatment of dog tumors using specie-specific angiogenesis inhibitors, thereby minimizing the risk of evoking immune responses under repeated administration. Finally, spontaneous canine tumors are very similar to their human correlates in histopathologic and biologic behavior (MacEwen, 1990, Cancer Metastasis Rev 9(2): 125–36), therefore experimental results obtained from canine tumors will also provide valuable information for human cancer biology and treatment.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed:

1. An isolated nucleic acid molecule comprising a nucleotide sequence that encodes an endostatin consisting of:

a) a polypeptide as shown in SEQ ID NO: 2; or b) a polypeptide as shown in SEQ ID NO: 4.

2. An isolated nucleic acid molecule consisting of:

a) a nucleic acid as shown in SEQ ID NO: 1; or b) a nucleic acid as shown in SEQ ID NO: 3.

3. An isolated nucleic acid molecule comprising a complement of the nucleic acid molecule of any one of claims 1–2.

4. A vector comprising the nucleic acid of any one of claims 1–2.

5. An expression vector comprising the nucleic acid of any one of claims 1–2 operatively associated with a regulatory nucleic acid controlling the expression of the polypeptide encoded by said nucleic acid.

6. A host cell genetically engineered to contain the nucleic acid of any on of claims 1–2.

7. A host cell genetically engineered to express the nucleic acid of any one of claims 1–2 operatively associated with a regulatory nucleic acid controlling expression of the polypeptide encoded by said nucleic acid.

* * * * *

SEQUENCE LISTING

<160> NUMBER OF SEQ ID NOS: 15

<210> SEQ ID NO 1
<211> LENGTH: 829
<212> TYPE: DNA
<213> ORGANISM: CANINE

<400> SEQUENCE: 1

| | | | | | | |
|---|---|---|---|---|---|---|
| ccctggcggg | cagatgacat | cctggccggc | ccccgcgcc | tgctggaccc | ccagccctac | 60 |
| cccggggccc | cgcaccacgg | ctcctacgtg | cacttccagc | cggctcgccc | cactggtggg | 120 |
| cccgtccaca | cccacaccca | cacccaccag | gacttccagc | tggtgctgca | cctggtggcc | 180 |
| ctgaacagcc | cgcagccggg | cggcatgcga | ggcatccggg | gagcggactt | ccagtgcttc | 240 |
| cagcaggcgc | gcgccgcggg | gctggccggc | accttccggg | ccttcctgtc | gtcgcggctg | 300 |
| caggacctct | acagcatcgt | gcgccgcgcc | gaccgcaccg | gggtgcccgt | cgtcaacctc | 360 |
| agggacgagg | tgctcttccc | cagctgggag | gccttattct | cgggctccga | gggccagctg | 420 |
| aagcccgggg | cccgcatctt | ctctttcgac | ggcagagatg | tcctgcagca | ccccgcctgg | 480 |
| ccccggaaga | gcgtgtggca | cggctccgac | cccagcgggc | gccgcctgac | cgacagctac | 540 |
| tgcgagacgt | ggcggacgga | ggccccggcg | gccaccgggc | aggcgtcgtc | gctgctggcg | 600 |
| ggcaggctgc | tggagcagga | ggccgcgagc | tgccgccacg | ccttcgtggt | gctctgcatc | 660 |
| gagaacagcg | tcatgacctc | cttctccaag | tagggccgcg | cggcccacgg | acaggcgggg | 720 |
| gagggggcgc | ccgcaggagc | atccgccgcc | ccgggggggc | ctggccggga | cgcttgcctg | 780 |
| caccgtcacg | tttaatgtaa | tcctcaagaa | ataaaaggaa | gccaaagag | | 829 |

<210> SEQ ID NO 2
<211> LENGTH: 230
<212> TYPE: PRT
<213> ORGANISM: CANINE

<400> SEQUENCE: 2

Pro Trp Arg Ala Asp Asp Ile Leu Ala Gly Pro Pro Arg Leu Leu Asp
1               5                  10                  15

Pro Gln Pro Tyr Pro Gly Ala Pro His His Gly Ser Tyr Val His Phe
            20                  25                  30

Gln Pro Ala Arg Pro Thr Gly Gly Pro Val His Thr His Thr His Thr
        35                  40                  45

His Gln Asp Phe Gln Leu Val Leu His Leu Val Ala Leu Asn Ser Pro
    50                  55                  60

Gln Pro Gly Gly Met Arg Gly Ile Arg Gly Ala Asp Phe Gln Cys Phe
65                  70                  75                  80

Gln Gln Ala Arg Ala Ala Gly Leu Ala Gly Thr Phe Arg Ala Phe Leu
            85                  90                  95

Ser Ser Arg Leu Gln Asp Leu Tyr Ser Ile Val Arg Arg Ala Asp Arg
            100                 105                 110

Thr Gly Val Pro Val Val Asn Leu Arg Asp Glu Val Leu Phe Pro Ser
        115                 120                 125

Trp Glu Ala Leu Phe Ser Gly Ser Glu Gly Gln Leu Lys Pro Gly Ala
    130                 135                 140

Arg Ile Phe Ser Phe Asp Gly Arg Asp Val Leu Gln His Pro Ala Trp
145                 150                 155                 160

Pro Arg Lys Ser Val Trp His Gly Ser Asp Pro Ser Gly Arg Arg Leu

-continued

```
                165                 170                 175

Thr Asp Ser Tyr Cys Glu Thr Trp Arg Thr Glu Ala Pro Ala Ala Thr
            180                 185                 190

Gly Gln Ala Ser Ser Leu Leu Ala Gly Arg Leu Leu Glu Gln Glu Ala
        195                 200                 205

Ala Ser Cys Arg His Ala Phe Val Val Leu Cys Ile Glu Asn Ser Val
    210                 215                 220

Met Thr Ser Phe Ser Lys
225                 230


<210> SEQ ID NO 3
<211> LENGTH: 555
<212> TYPE: DNA
<213> ORGANISM: CANINE

<400> SEQUENCE: 3

cacacccacc aggacttcca gctggtgctg cacctggtgg ccctgaacag cccgcagccg      60

ggcggcatgc gaggcatccg gggagcggac ttccagtgct tccagcaggc gcgcgccgcg     120

gggctggccg gcaccttccg ggccttcctg tcgtcgcggc tgcaggacct ctacagcatc     180

gtgcgccgcg ccgaccgcac cggggtgccc gtcgtcaacc tcagggacga ggtgctcttc     240

cccagctggg aggccttatt ctcgggctcc gagggccagc tgaagcccgg ggcccgcatc     300

ttctctttcg acggcagaga tgtcctgcag caccccgcct ggccccggaa gagcgtgtgg     360

cacggctccg accccagcgg gcgccgcctg accgacagct actgcgagac gtggcggacg     420

gaggccccgg cggccaccgg gcaggcgtcg tcgctgctgg cgggcaggct gctggagcag     480

gaggccgcga gctgccgcca cgccttcgtg gtgctctgca tcgagaacag cgtcatgacc     540

tccttctcca agtag                                                      555


<210> SEQ ID NO 4
<211> LENGTH: 184
<212> TYPE: PRT
<213> ORGANISM: CANINE

<400> SEQUENCE: 4

His Thr His Gln Asp Phe Gln Leu Val Leu His Leu Val Ala Leu Asn
1               5                   10                  15

Ser Pro Gln Pro Gly Gly Met Arg Gly Ile Arg Gly Ala Asp Phe Gln
            20                  25                  30

Cys Phe Gln Gln Ala Arg Ala Ala Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Thr Gly Val Pro Val Val Asn Leu Arg Asp Glu Val Leu Phe
65                  70                  75                  80

Pro Ser Trp Glu Ala Leu Phe Ser Gly Ser Glu Gly Gln Leu Lys Pro
                85                  90                  95

Gly Ala Arg Ile Phe Ser Phe Asp Gly Arg Asp Val Leu Gln His Pro
            100                 105                 110

Ala Trp Pro Arg Lys Ser Val Trp His Gly Ser Asp Pro Ser Gly Arg
        115                 120                 125

Arg Leu Thr Asp Ser Tyr Cys Glu Thr Trp Arg Thr Glu Ala Pro Ala
    130                 135                 140

Ala Thr Gly Gln Ala Ser Ser Leu Leu Ala Gly Arg Leu Leu Glu Gln
145                 150                 155                 160
```

-continued

```
Glu Ala Ala Ser Cys Arg His Ala Phe Val Val Leu Cys Ile Glu Asn
                165                 170                 175

Ser Val Met Thr Ser Phe Ser Lys
            180


<210> SEQ ID NO 5
<211> LENGTH: 27
<212> TYPE: DNA
<213> ORGANISM: MURINE

<400> SEQUENCE: 5

ccctggcggg cagatgacat cctggcc                                      27


<210> SEQ ID NO 6
<211> LENGTH: 35
<212> TYPE: DNA
<213> ORGANISM: MURINE

<400> SEQUENCE: 6

ctctttggct tccttttatt tcttgaggat tacat                             35


<210> SEQ ID NO 7
<211> LENGTH: 33
<212> TYPE: DNA
<213> ORGANISM: CANINE

<400> SEQUENCE: 7

gattaagctt cacacccacc aggacttcca gct                               33


<210> SEQ ID NO 8
<211> LENGTH: 34
<212> TYPE: DNA
<213> ORGANISM: CANINE

<400> SEQUENCE: 8

ctgagaattc ctacttggag aaggaggtca tgac                              34


<210> SEQ ID NO 9
<211> LENGTH: 32
<212> TYPE: DNA
<213> ORGANISM: MURINE

<400> SEQUENCE: 9

ctagagatct catactcatc aggactttca gc                                32


<210> SEQ ID NO 10
<211> LENGTH: 32
<212> TYPE: DNA
<213> ORGANISM: MURINE

<400> SEQUENCE: 10

gctagtcgac ctatttggag aaagaggtca tg                                32


<210> SEQ ID NO 11
<211> LENGTH: 184
<212> TYPE: PRT
<213> ORGANISM: CHICKEN

<400> SEQUENCE: 11

His Val His Gln Asp Phe Gln Pro Ala Leu His Leu Val Ala Leu Asn
1               5                   10                  15

Thr Pro Leu Ser Gly Gly Met Arg Gly Ile Arg Gly Ala Asp Phe Gln
```

-continued 20 25 30

Cys Phe Gln Gln Ala Arg Gln Val Gly Leu Ala Gly Thr Phe Arg Ala
35 40 45

Phe Leu Ser Ser Arg Leu Gln Asp Leu Tyr Ser Ile Val Arg Arg Ala
50 55 60

Asp Arg Thr Ala Val Pro Ile Val Asn Leu Arg Asp Glu Val Leu Phe
65 70 75 80

Ser Asn Trp Glu Ala Leu Phe Thr Gly Ser Glu Ala Pro Leu Arg Ala
85 90 95

Gly Ala Arg Ile Leu Ser Phe Asp Gly Arg Asp Ile Leu Gln Asp Ser
100 105 110

Ala Trp Pro Gln Lys Ser Ile Trp His Gly Ser Asp Ala Lys Gly Arg
115 120 125

Arg Leu Pro Glu Ser Tyr Cys Glu Ala Trp Arg Thr Asp Glu Arg Gly
130 135 140

Thr Ser Gly Gln Ala Ser Ser Leu Ser Ser Gly Lys Leu Leu Glu Gln
145 150 155 160

Ser Ala Ser Ser Cys Gln His Ala Phe Val Val Leu Cys Ile Glu Asn
165 170 175

Ser Phe Met Thr Ala Ala Lys Lys
180

<210> SEQ ID NO 12
<211> LENGTH: 183
<212> TYPE: PRT
<213> ORGANISM: HUMAN

<400> SEQUENCE: 12

His Ser His Arg Asp Phe Gln Pro Val Leu His Leu Val Ala Leu Asn
1 5 10 15

Ser Pro Leu Ser Gly Gly Met Arg Gly Ile Arg Gly Ala Asp Phe Gln
20 25 30

Cys Phe Gln Gln Ala Arg Ala Val Gly Leu Ala Gly Thr Phe Arg Ala
35 40 45

Phe Leu Ser Ser Arg Leu Gln Asp Leu Tyr Ser Ile Val Arg Arg Ala
50 55 60

Asp Arg Ala Ala Val Pro Ile Val Asn Leu Lys Asp Glu Leu Leu Phe
65 70 75 80

Pro Ser Trp Glu Ala Leu Phe Ser Gly Ser Glu Gly Pro Leu Lys Pro
85 90 95

Gly Ala Arg Ile Phe Ser Phe Asp Gly Lys Asp Val Leu Arg His Pro
100 105 110

Ile Trp Pro Gln Lys Ser Val Trp His Gly Ser Asp Pro Asn Gly Arg
115 120 125

Arg Leu Thr Glu Ser Tyr Cys Glu Thr Trp Arg Thr Glu Ala Pro Ser
130 135 140

Ala Thr Gly Gln Ala Ser Ser Leu Leu Gly Gly Arg Leu Leu Gly Gln
145 150 155 160

Ser Ala Ala Ser Cys His His Ala Tyr Ile Val Leu Cys Ile Glu Asn
165 170 175

Ser Phe Met Thr Ala Ser Lys
180

<210> SEQ ID NO 13
<211> LENGTH: 184

-continued

```
<212> TYPE: PRT
<213> ORGANISM: MURINE

<400> SEQUENCE: 13

His Thr His Gln Asp Phe Gln Pro Val Leu His Leu Val Ala Leu Asn
1               5                   10                  15

Thr Pro Leu Ser Gly Gly Met Arg Gly Ile Arg Gly Ala Asp Phe Gln
            20                  25                  30

Cys Phe Gln Gln Ala Arg Ala Val Gly Leu Ser Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Gly Ser Val Pro Ile Val Asn Leu Lys Asp Glu Val Leu Ser
65                  70                  75                  80

Pro Ser Trp Asp Ser Leu Phe Ser Gly Ser Gln Gly Gln Leu Gln Pro
                85                  90                  95

Gly Ala Arg Ile Phe Ser Phe Asp Gly Arg Asp Val Leu Arg His Pro
            100                 105                 110

Ala Trp Pro Gln Lys Ser Val Trp His Gly Ser Asp Pro Ser Gly Arg
        115                 120                 125

Arg Leu Met Glu Ser Tyr Cys Glu Thr Trp Arg Thr Glu Thr Thr Gly
    130                 135                 140

Ala Thr Gly Gln Ala Ser Ser Leu Leu Ser Gly Arg Leu Leu Glu Gln
145                 150                 155                 160

Lys Ala Ala Ser Cys His Asn Ser Tyr Ile Val Leu Cys Ile Glu Asn
                165                 170                 175

Ser Phe Met Thr Ser Phe Ser Lys
            180


<210> SEQ ID NO 14
<211> LENGTH: 32
<212> TYPE: DNA
<213> ORGANISM: CANINE

<400> SEQUENCE: 14

ctagagatct cacacccacc aggacttcca gc                                  32


<210> SEQ ID NO 15
<211> LENGTH: 34
<212> TYPE: DNA
<213> ORGANISM: CANINE

<400> SEQUENCE: 15

cgtagtcgac ctacttggag aaggaggtca tgac                                34
```